(12) United States Patent
Sullivan

(10) Patent No.: US 7,736,771 B2
(45) Date of Patent: Jun. 15, 2010

(54) APPARATUS AND METHOD FOR GENERATING AND USING MULTI-DIRECTION DC AND AC ELECTRICAL CURRENTS

(76) Inventor: John Timothy Sullivan, 11339 Barley Field Way, Marriottsville, MD (US) 21104-1346

( * ) Notice: Subject to any disclaimer, the term of this patent is extended or adjusted under 35 U.S.C. 154(b) by 1082 days.

(21) Appl. No.: 11/342,797

(22) Filed: Jan. 31, 2006

(65) Prior Publication Data

US 2006/0251929 A1 Nov. 9, 2006

Related U.S. Application Data

(62) Division of application No. 10/411,307, filed on Apr. 11, 2003, now Pat. No. 7,041,203.

(51) Int. Cl.
*H01M 14/00* (2006.01)
*H01M 4/58* (2010.01)
*H01G 9/28* (2006.01)

(52) U.S. Cl. .............................. 429/3; 429/218.2; 429/7; 361/522

(58) Field of Classification Search ....................... 429/3
See application file for complete search history.

(56) References Cited

U.S. PATENT DOCUMENTS

| | | | | |
|---|---|---|---|---|
| 5,558,757 A | * | 9/1996 | Hubel | 205/96 |
| 5,712,054 A | * | 1/1998 | Kejha | 429/21 |
| 2003/0214269 A1 | * | 11/2003 | Shiue et al. | 320/166 |

* cited by examiner

*Primary Examiner*—Patrick Ryan
*Assistant Examiner*—Brent Thomas
(74) *Attorney, Agent, or Firm*—Bacon & Thomas, PLLC

(57) ABSTRACT

Multi-directional currents are generated in a medium by cyclically reversing the direction of a conventional current applied to at least one of at least two electrodes so that an electromotive force (EMF) pulse travels from side of the electrode to the other, changing the direction of current in the medium. The multi-directional currents may be used to accelerate electrolytic processes such as generation of hydrogen by water electrolysis, to sterilize water for drinking, to supply charging current to a battery or capacitor, including a capacitive thrust module, in a way that extends the life and/or improves the performance of the battery or capacitor, to increase the range of an electromagnetic projectile launcher, and to increase the light output of a cold cathode light tube, to name just a few of the potential applications for the multi-directional currents.

18 Claims, 22 Drawing Sheets

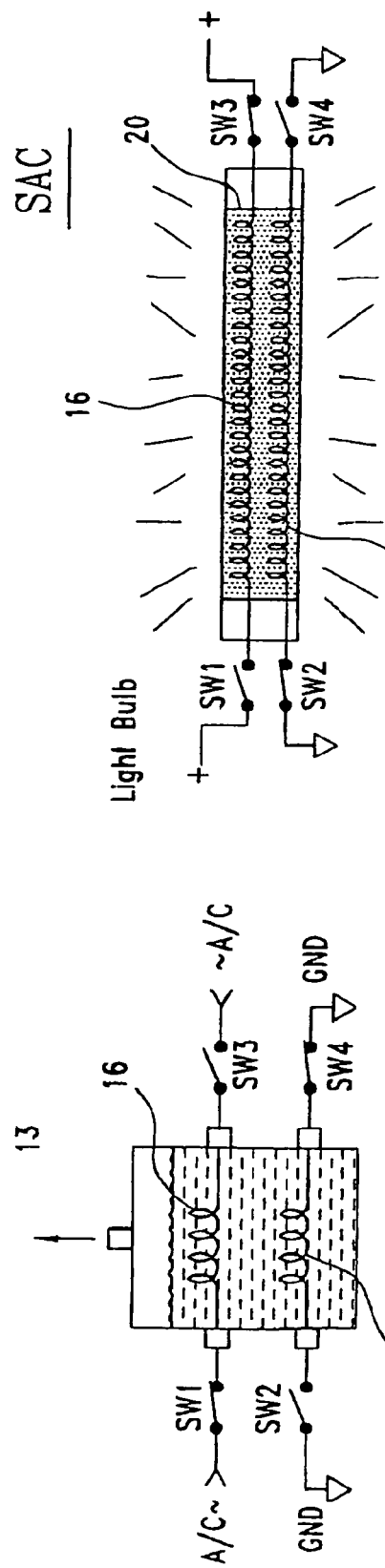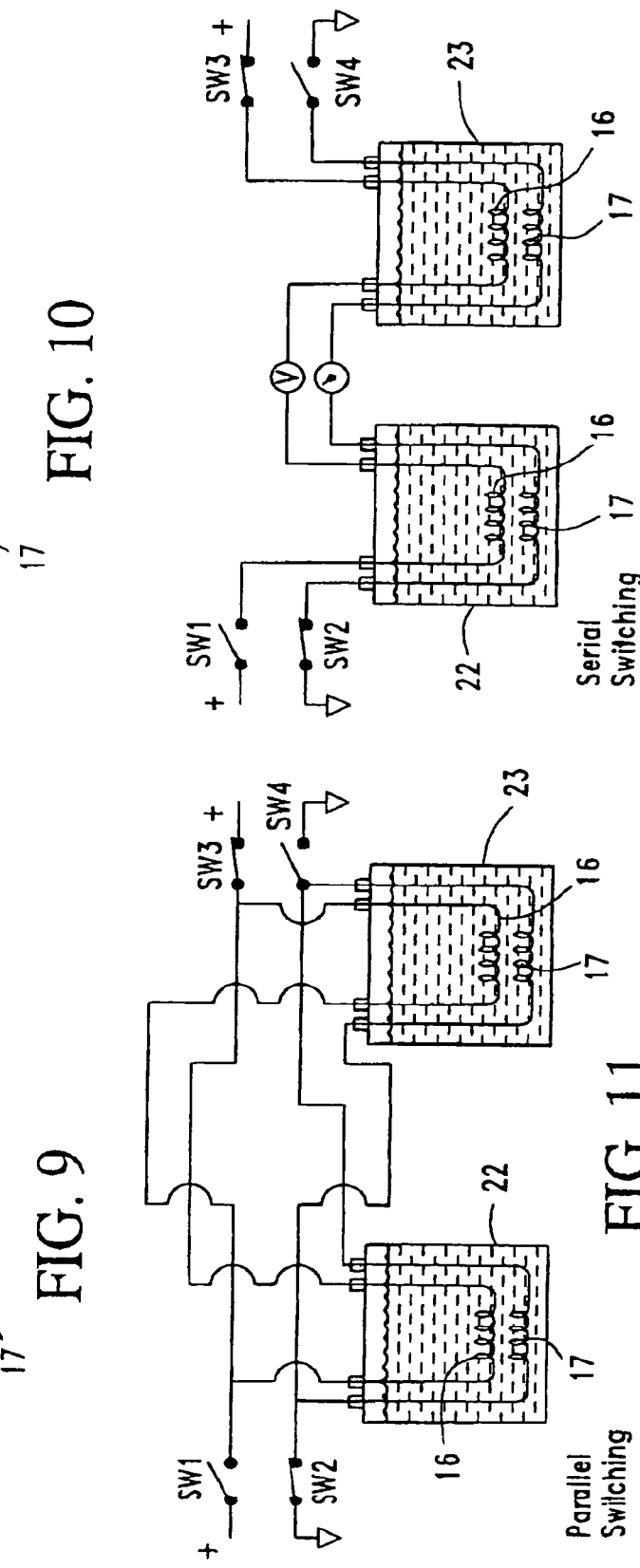

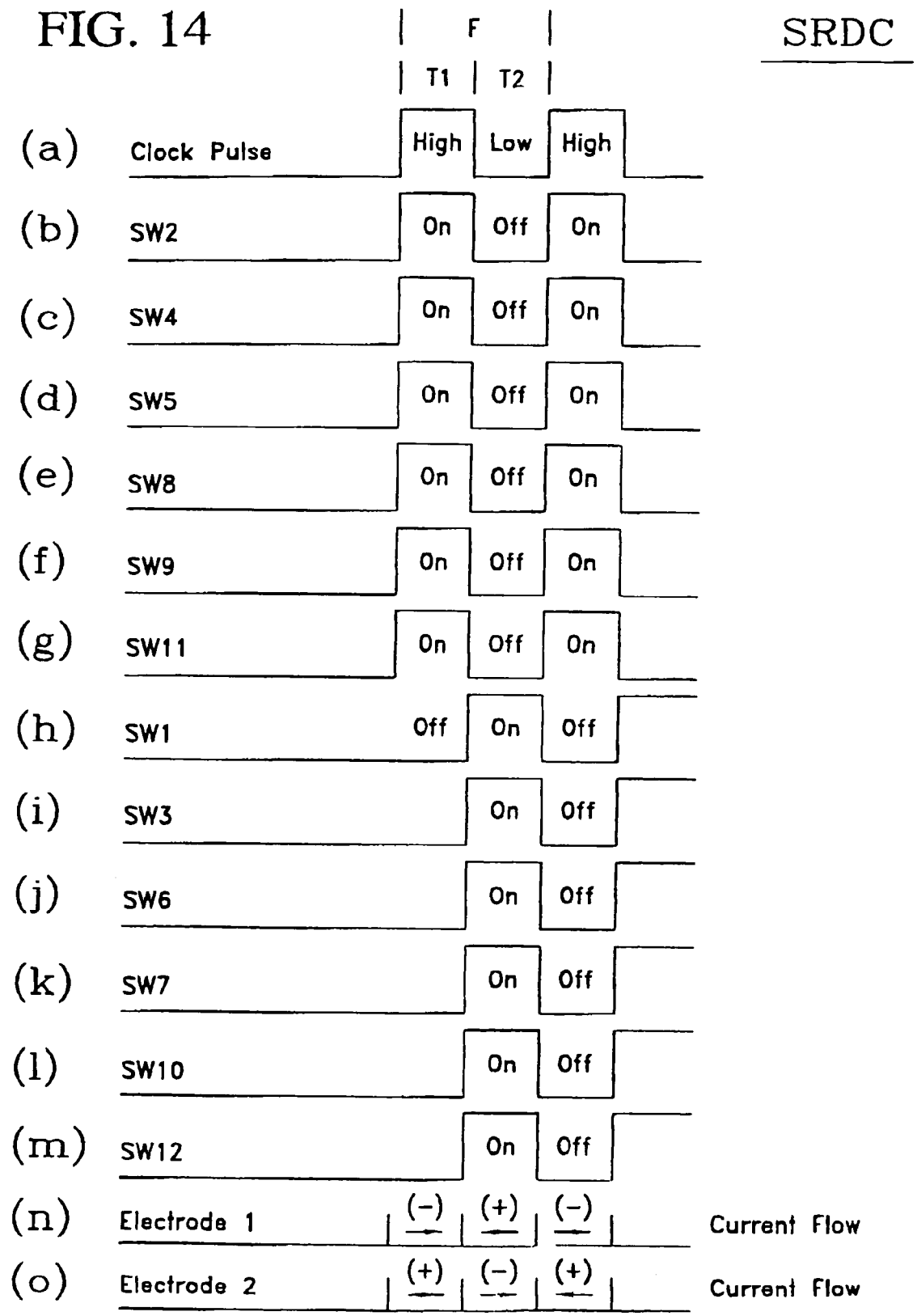

SRDC/SDC

SAC
COLD CATHODE LIGHT

Sully Direct Current

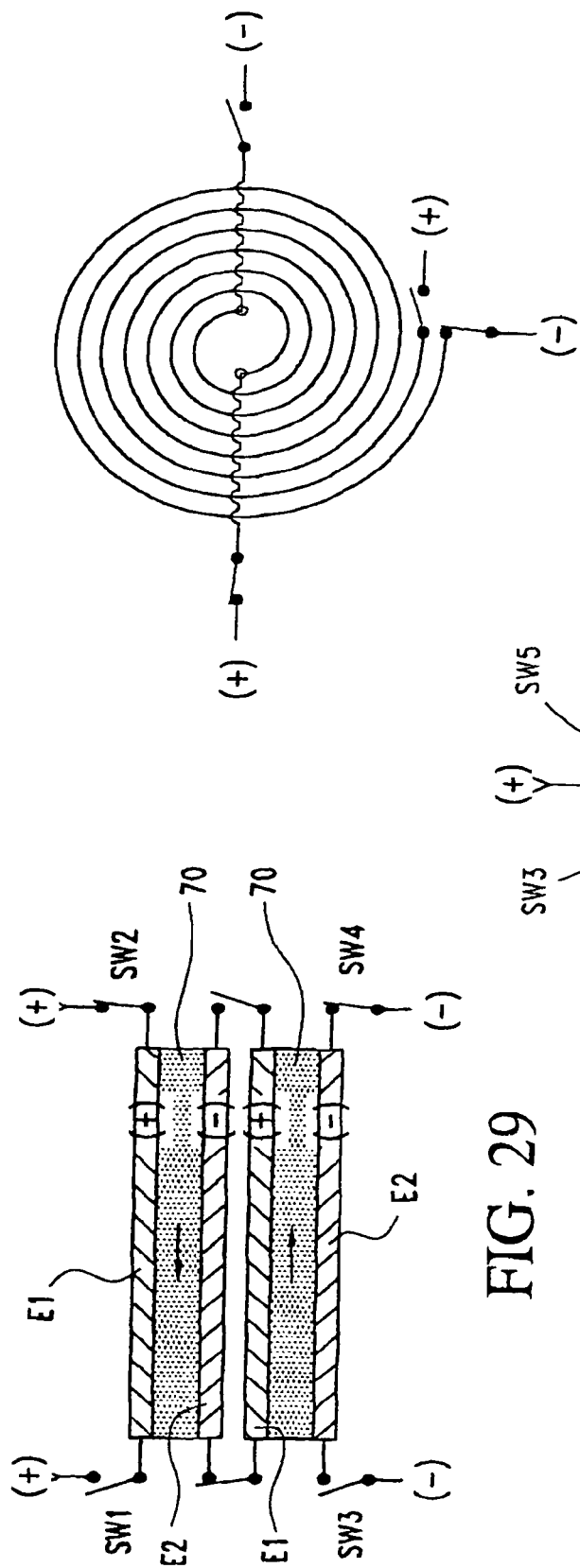
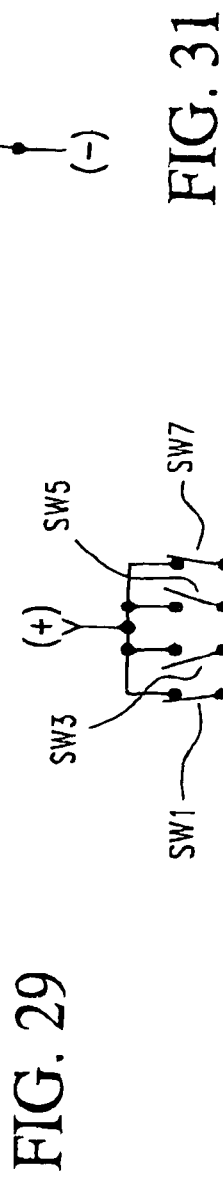
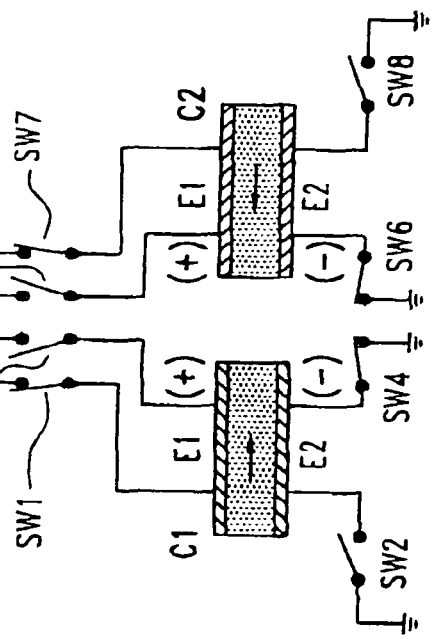
FIG. 29
FIG. 30
FIG. 31

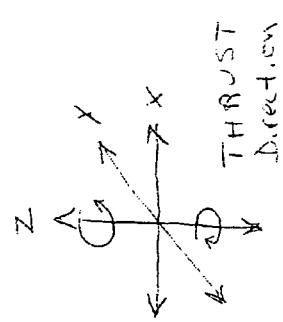
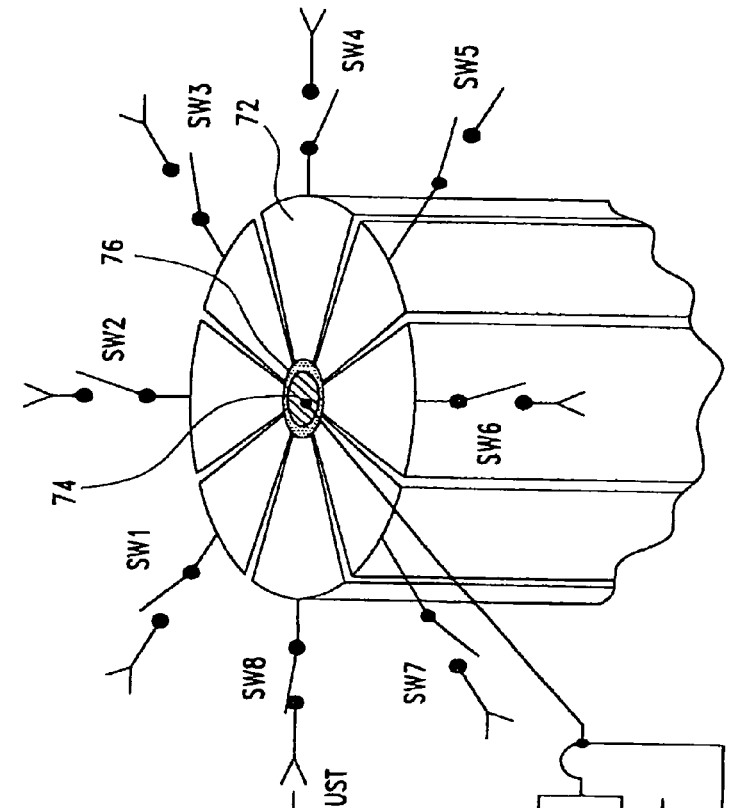
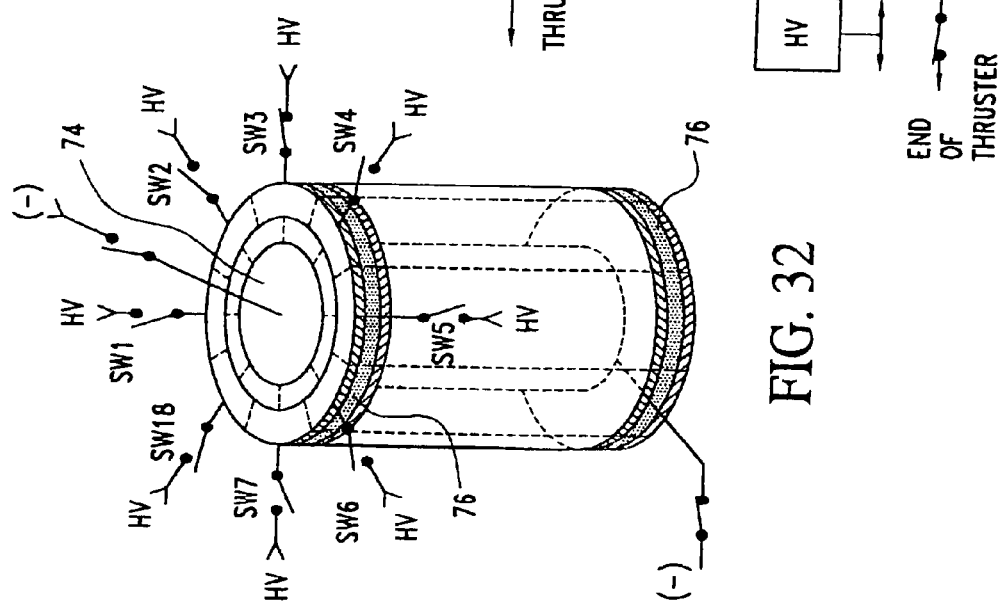
FIG. 32
FIG. 33

APPARATUS AND METHOD FOR GENERATING AND USING MULTI-DIRECTION DC AND AC ELECTRICAL CURRENTS

This application is a Division of U.S. patent application Ser. No. 10/411,307, filed Apr. 11, 2003 now U.S. Pat. No. 7,041,203.

BACKGROUND OF THE INVENTION

1. Field of the Invention

This invention relates to multi-directional, reciprocating electrical currents. The invention also relates to an apparatus and method for generating the multi-directional currents, and to applications of the generating apparatus and method.

The multi-directional currents of the invention are generated in a current carrying medium by cyclically reversing the direction of a conventional current applied to at least one of a plurality of electrodes, so that an electromotive force (EMF) pulse travels from one side of the at least one electrode to the other, changing the direction of current flowing through the medium between two or more electrodes.

The multi-directional electric currents have the effect of accelerating processes that rely on interaction between a current and the medium that carries the current, and of eliminating asymmetries that can lead to scaling or premature wear in batteries and other electrolytic systems. The medium that carries the multi-dimensional currents may be an electrolyte, gas, gel, semiconductor, or any other medium capable of carrying current between two electrodes, and having at least two dimensions so as to enable variation in the current direction.

By way of example and not limitation, the multi-directional electrical currents of the invention may be used to (i) increase the efficiency of hydrogen generation by electrolysis of water (while at the same time preventing scaling and purifying the water), (ii) extend the life of batteries such as nickel-metal hydride cells, and of capacitors, by symmetrically charging and discharging the batteries or capacitors, (iii) provide a power source for electromagnetic projectile weapons and similar devices, and (iv) increase the efficiency of plasma generation or light conversion in cold cathode systems.

Other potential applications of the multi-directional electric currents of the invention, and of the apparatus and method for generating the currents, include computers, communications, drug and chemical development, medical treatment of cancers, anti-gravity experiments, transportation, energy, water treatment, genetic research in humans, plants, and animals, and aeronautical propulsion systems, as well as fuel cell and PEM electrolysis systems utilizing proton exchange membranes and catalyst materials.

2. Description of Related Art

A. Basic Principle of Invention

The basic principle underlying the multi-directional currents of the invention may be understood from FIGS. 1A-1B. FIG. 1A shows the situation when electrode currents $i_{E1}$ and $i_{E2}$ in electrodes E1 and E2 are initially reversed, creating EMF or voltage pulses, edges, waves, or spikes that travel from left to right in the top electrode E1 and from right to left in the bottom electrode E2. The current $i_s$ between the electrodes flows from the top electrode E1 to E2, but changes direction as the current $i_s$ follows the respective EMF pulses or voltage spikes as they propagate from left to right through electrode E1 and from right to left through electrode E2. Eventually, as shown in FIG. 1B, the current flows from top right to bottom left, at which point the currents in the respective electrodes are again reversed to cause EMF or voltage pulses, waves, edges, or spikes to propagate in the opposite direction. As a result, the current $i_s$ can be caused to reciprocate or continuously change direction in an oscillating or cyclical manner within the current-carrying medium between the electrodes. If $i_{E1}$ and $i_{E2}$ are DC currents, the electrodes can be kept at a constant potential so that the net current direction remains constant even though the instantaneous current direction changes continuously or periodically, enabling the direction-changing current $i_s$ to be used in electrolytic processes that require direct current. Alternatively, $i_{E1}$, and $i_{E2}$ may be alternating currents, pulsed DC currents, or polarity-reversing DC currents. In addition, a similar but smaller variation in the direction of current will occur if the direction-reversing conventional current is applied to just one of the electrodes and the second electrode has a relatively small area.

The invention may thus be characterized as a method and apparatus of generating multi-directional currents in a medium by reversing the direction of electron flow in at least one of a pair of electrodes. If the voltages applied to the electrodes are DC voltages, then the multi-directional currents have characteristics of DC currents, and if the voltages applied to the electrodes are two or three phase AC voltages, then the multi-directional currents have characteristics of AC currents. However, unlike conventional DC and AC currents, the currents generated by the method and apparatus of the invention move or rotate. If the electrodes are one-dimensional wires, then the currents rotate in two-directions. If the electrodes themselves move, or extend over two or three-dimensions, for example a plane or a curved plane, then the currents will move in three-dimensions.

B. Conventional Electric Currents

There are two types of conventional electrical currents and corresponding voltages, neither of which changes direction in the manner of the present invention. The first, direct current (DC), was already well known when Benjamin Franklin performed his famous kite experiment in 1752 to prove that lighting was a form of electricity, while the second, alternating current, came into widespread use after Nikola Tesla invented the first alternating current motor in 1888 (U.S. Pat. No. 555,190).

Both direct and alternating voltages can be applied to electrodes for the purpose of causing a current to flow through a medium between the electrodes. However, the voltages are conventionally applied across the electrodes so that the resulting inter-electrode current follows a fixed, albeit reversible, path between the electrodes, irrespective of the type of medium or geometry of the electrodes. This is clearly the case in systems having only a single terminal for each electrode, and in systems having multiple terminals but no switching circuit.

It is of course possible to periodically reverse the polarity of currents applied to the electrodes in such a system, and a number of systems have been proposed for doing so, including the systems disclosed in the patents discussed below. However, none of the previously proposed systems involves changing the direction of current in a single one, or both, of the electrodes so as to vary the direction of current flowing between the electrodes by other than 180°.

The invention in its broadest form consists of the above-described multi-directional currents, and apparatus and methods for generating the currents. However, an important aspect of the invention is the numerous applications in which the unique properties of the multi-directional currents may be exploited. These applications include, but are not limited to, the following:

C. Hydrogen Generation By Electrolysis of Water

One of the applications of the invention is electrolysis of water to generate hydrogen, or hydrogen and oxygen, for use in fuel cells and other essentially pollution-free hydrogen-driven power sources. This application is of particular importance because it offers a solution to the problem of generating, storing, and transporting the hydrogen.

Hydrogen fuel cells, in particular, have the potential to provide a completely non-polluting power source of electricity, not only for vehicles but also for electricity generation in general, but have been limited by lack of a safe distribution system for the hydrogen, and by the costs of generating the hydrogen in the first place. While it has long been known that hydrogen may be generated by applying a direct current to water, the rate of hydrogen generation is too low to provide a practical hydrogen source for mass distribution. As a result, hydrogen for mass consumption is currently produced from fossil fuels at relatively high energy costs relative to the energy value of the hydrogen produced. However, if sufficient hydrogen could be produced by water electrolysis to provide an on-board hydrogen generator for a vehicle or electric power plant, so as to generate just enough hydrogen to supply the fuel cells, then the need for a distribution system and hydrogen storage would be eliminated.

Power or propulsion systems that use water electrolysis in combination with hydrogen fuel cells to generate the hydrogen necessary to power the fuel cells are known as regenerative electrochemical cell or systems, an example of which is disclosed in U.S. Published Patent Application No. 2002/0051898. Despite their theoretical promise, however, similar systems have yet to offer a practical alternative to fossil fuels. It is believed that a regenerative system can only attain widespread acceptance if the efficiency of hydrogen production is increased. The multi-directional currents of the invention offer the potential for providing such an increase in water electrolysis efficiency.

The way that the invention increases water electrolysis efficiency is by using the applied electric current to not only pull the water molecules apart at the cathode, as in a conventional electrolysis system, but to add a shearing force that helps break apart the ionic bonds between the oxygen and hydrogen atoms. The effect is similar to separating a pair of magnets by sliding them perpendicularly rather than pulling them apart. In conventional electrolysis, the water molecules tend to align with the positive and negative electrodes in the manner illustrated in FIG. 2, so that the ionic bonds are at a constant angle of 54.74° relative to the direction of current flow. This is not the optimal angle for breaking the ionic bonds and disassociating the hydrogen atoms from the oxygen atoms. In the set-up illustrated in FIG. 3, on the other hand, the molecules are subject to a continuously changing current direction, which applies both tensile and shearing forces to the molecules, substantially increasing the rate of disassociation. In addition, the electrodes can be arranged in coils to add magnetic forces that further expedite disassociation.

It will be noted that the set-up illustrated in FIG. 2 does not reverse the polarities of the electrodes, which would only slow the electrolysis process due to energy lost in flipping the water molecules. The multi-directional currents are not alternating currents, but rather in this embodiment are direct currents. Systems that reverse the polarities of electrodes have previously been used in electrolysis, but the currents are uni-directional and the reversals are carried out at relatively long intervals so that the effect is that of a conventional DC current. The purpose of the reversals is to reduce scaling by switching between anodic and cathodic reactions at the respective electrodes. This can also be accomplished with the present invention, by reversing the polarities of the electrodes in addition to reversing current directions in the individual electrodes. Examples of electrolysis apparatus (though not necessarily a hydrogen generating water electrolysis apparatus) that reverse DC potential between two electrodes are disclosed in U.S. Pat. Nos. 6,258,250, 6,174,419, and 1,402,986, and in U.S. Published Patent Application No. 2002/0074237.

Periodic reversal of the polarities of electrodes has also been used in electrolytic water purification systems. The periodically reversed currents can be used to directly destroy bacteria as in U.S. Pat. No. 3,865,710, or to expedite the release of electrolytic reaction by-products such as metal ions, as disclosed in U.S. Pat. Nos. 6,241,861; 5,062,940; 4,908,109 (entitled "Electrolytic Purification System Utilizing Rapid Reverse Current Plating Electrodes"); U.S. Pat. Nos. 4,734,176; 4,525,253; and 3,654,119.

These systems are not to be confused with the system of the invention, which changes the direction of currents but does not necessarily change their polarity. However, the effects of the direction-reversing currents, and/or released ions, on bacteria and other micro-organisms can be utilized and even increased by the present invention, i.e., the currents of the present invention can be used not only for electrolysis of water to generate hydrogen, but also to purify the water. Unlike the currents disclosed in the water purification references, which cannot be used for hydrogen generation, the present invention combines generation of hydrogen with water purification so that, for example, a power plant that included hydrogen generation cells supplied with river water would also have the effect of cleaning the river water, serving as a source not only of electricity but also of potable water.

D. Charging of Nickel-Metal Hydride Foam Batteries

Although especially useful for water electrolysis, the present invention is not limited to a particular electrolyte, electrolytic process, or electrolytic cell configuration. In another application of the invention, the multi-direction currents of the invention are applied to the electrodes of a battery containing an electrolyte. This application of the invention takes advantage of the reversing currents in the electrodes to reduce the wear and tear of friction and heat caused in conventional batteries by current moving from one post down the length of the electrode.

In the case of batteries containing nickel metal hydride, as disclosed in U.S. Pat. No. 6,413,670, additional advantages of using the method and apparatus of the invention to charge the battery an increase in the hydrogen generated during the charging process, which may be captured by utilizing the principles of the gas capture system described in U.S. patent application Ser. No. 10/314,987 by the present inventor, now U.S. Pat. No. 6,890,410. Furthermore, the use of multi-directional currents may improve the ability of the foam to absorb hydrogen through the hydride substrate in a manner analogous to shaking of a screen to expedite passage of granular materials.

E. Capacitors

The apparatus and method of the invention can also be applied to capacitors and capacitive systems, which have similar fundamental problems of fast charging heat losses and discharge heat wear.

An example of capacitive systems to which the principles of the invention may be applied are the thrust generating systems disclosed in U.S. Pat. Nos. 6,317,310, 3,022,430, and 2,949,550, which use the electrostatic force between asymmetric capacitor plates to generate a thrust force. The EMF voltage spikes utilized by the present invention amplify the high voltage as the current changes direction to improve thrust performance. In addition, the magnetic field switching multi-directional high voltage currents may be computer controlled on the surface of the capacitor module's thrust plates or thrust tubes to change the direction and speed of the module, and the polarity of the currents may be controlled to change the direction of thrust. Thrust, pitch, roll, and yaw can be controlled by multiple such capacitor modules.

F. Cold Cathode Light and Plasma Generators

The principles of the invention are not limited to electrolyte materials, but may be applied to any medium capable of carrying charges between a pair of electrodes, including not only electrolytes, but also gases, gels, and semi-conductors. For example, when applied to a cold cathode light, reversing the current direction in the electrodes to change the direction of the excitation current between the electrodes will cause the ionized gas to produce more electrons, and thereby produce a brighter glow.

Similarly, in systems that generate plasma by passing a gas between electrodes, the multi-direction currents of the invention will increase the rate of plasma production relative to direct current systems, and those that use a single electrode polarity reversing switch applied to a single terminal on each of the electrodes of the plasma generator, as disclosed in U.S. Pat. No. 6,222,321.

G. Electro-Magnetic Devices

According to Lenz's law, a changing electrical current generates a magnetic flux having a magnitude that is proportional to the rate of change of the current. In the present invention, which utilizes reversing direct currents in the electrodes, the energy resulting from the above-described EMF or voltage pulses, edges, waves, or spikes can also be utilized to generate a corresponding magnetic field, which in turn can be used to drive a projectile in an electro-magnetic gun, or a piston.

In addition, such systems can be made regenerative by capturing hydrogen generated during charging and using the hydrogen to power a fuel cell, which in turn charges a battery for accumulating energy to be supplied to the electrode coils when the weapon is fired or the piston is to be operated.

H. Computing Devices

By adding two inputs and outputs to the conventional electrolytic cell, the apparatus of the invention may also be used in logic circuits and computing devices. U.S. Pat. No. 3,172,083 discloses an electrolytic memory utilizing three electrodes, but each electrode only has a single input, and thus the resulting storage cell has no advantage over conventional silicon memory devices.

I. Medical Devices

The multi-directional currents of the invention may also be applied to a variety of medical devices, including x-ray machines and various devices for treating tissues by electrical currents and/or magnetic fields.

SUMMARY OF THE INVENTION

It is accordingly a first objective of the invention to provide an apparatus and method that utilizes electricity in a more efficient manner in order to conserve energy resources and protect the environment.

It is a second objective of the invention to provide an improved electrical current generating apparatus and method which accelerate electrolytic and cathodic processes, including generation of hydrogen.

It is a third objective of the invention to provide an improved electrical current generating apparatus and method capable of more efficiently sterilizing water.

It is a fourth objective of the invention to provide an improved electrical current generating apparatus and method capable of more efficiently charging a battery.

It is a fifth objective of the invention to provide an improved electromagnetic device capable of utilizing the counter-EMF generating upon reversal of an electric current.

It is a sixth objective of the invention to provide a multi-dimensional electrical current having the property of changing direction as it flows from one electrode to the other, with or without changes in polarity.

It is a seventh objective of the invention to provide a system and method for generating a direct current that changes current direction with at least two ground switching paths and two positive connections in a parallel switching relationship back and forth, in phase or out of phase.

It is an eighth objective of the invention to provide a direct current that changes directions while the polarity of the electrodes changes back and forth.

It is a ninth objective of the invention to provide an alternating current with a sine wave in a parallel relationship with earth ground or neutral which switches from one end to the other to control the direction of current from the ground or neutral.

These objectives are achieved, in accordance with the principles of a preferred embodiment of the invention, by providing an apparatus having at least two spaced electrodes, a current carrying medium between the electrodes, and at least two terminals at each end of each of the electrodes, for a total of at least four terminals, to which a direction-reversing direct or alternating current is applied.

The electrodes may have a variety of shapes, including wires, coils, planar, or curved structures. The direction reversal may be effected by an electromechanical switching network, solid state, photonic or mechanical switches, and so forth, including the current reversing circuitry disclosed in the above-cited patents. In addition, the currents applied to the electrodes may include alternating as well as direct currents, the present invention being distinguished in that the current reversing circuitry is applied to opposite ends of at least one, and preferably each, of the two electrodes, so that reversal of the currents occurs within the electrodes, as opposed to within the current carrying medium between the electrodes (although, as described below, the direction of the multidirectional current within the current carrying medium may also be reversed by switching the polarity of the electrodes in addition to reversal of the current within the electrodes).

In the case of an electrolytic process, the multidirectional currents have the effect of substantially increasing the efficiency by which bonds in the electrolyte are broken, thereby providing an enhanced electrolysis method for producing hydrogen, oxygen, and other gases, and at the same can be arranged to purify the remaining electrolyte.

When the electrodes are in the form of coils, then a magnetic field is generated that may further accelerate certain electrolytic processes such as the generation of hydrogen, with or without using the multi-directional currents. While the advantages of multi-directional currents apply to coil-shaped electrodes, advantages may also be obtained by operating electrolytic cells and other devices with coil-shaped electrodes in DC, pulsed DC, reversing polarity, and AC modes, in addition to various multi-directional current modes.

The new types of currents and corresponding voltages can be used to power a new generation of batteries, capacitors, motors, light bulbs, and plasma generators, as well as for hydrogen and oxygen generation, and further may be applied to applications ranging from electroplating of metals and plastics to transportation, to name just a few of the potential applications. In the field of medicine, the currents can be used in x-ray machines, to destroy cancer cells by placing a patient inside a coil to which the currents are supplied at frequencies known to kill cancer cells without affecting non-cancerous tissue, and in other devices that involve application of electrical currents and/or magnetic fields to tissues. DNA electrophoresis can be performed by using ADC instead of DC by running DNA gel samples from both ends of the gel plate instead of one. 46% of the planet's population doesn't have electricity or fresh drinking water due to the cost of infrastructure required to supply power lines and water connections. The new clean and cheap voltages (which may be referred to as SULLY VOLTAGES™ after the Inventor, John Sullivan) will revolutionize third world countries by supplying cheap power and fresh drinking water without petroleum based fuel oil.

BRIEF DESCRIPTION OF THE DRAWINGS

FIGS. 6-9 are schematic diagrams showing variations of the electrolysis cell illustrated in FIG. 4.

FIG. 10 is a schematic diagram of a lighting element constructed in accordance with the principles of the invention.

FIGS. 11-13 show further variations of the electrolysis cell illustrated in FIG. 4.

FIG. 14 is a timing diagram for the polarity-reversing electrolysis cell illustrated in FIG. 13.

FIG. 29 is a cross-sectional view of two capacitors connected in series according to the principles of the invention.

FIG. 30 is a schematic diagram of two capacitors connected in parallel according to the principles of the invention.

FIG. 31 is a schematic diagram of a jelly roll capacitor configuration.

FIG. 32 is a perspective view of a capacitive thrust module constructed in accordance with the principles of the invention.

FIG. 33 is a plan view of the thrust module of FIG. 33, illustrating the manner in which currents are controlled on the surface of one of the capacitor plates.

DETAILED DESCRIPTION OF THE PREFERRED EMBODIMENTS

Figure 1A:
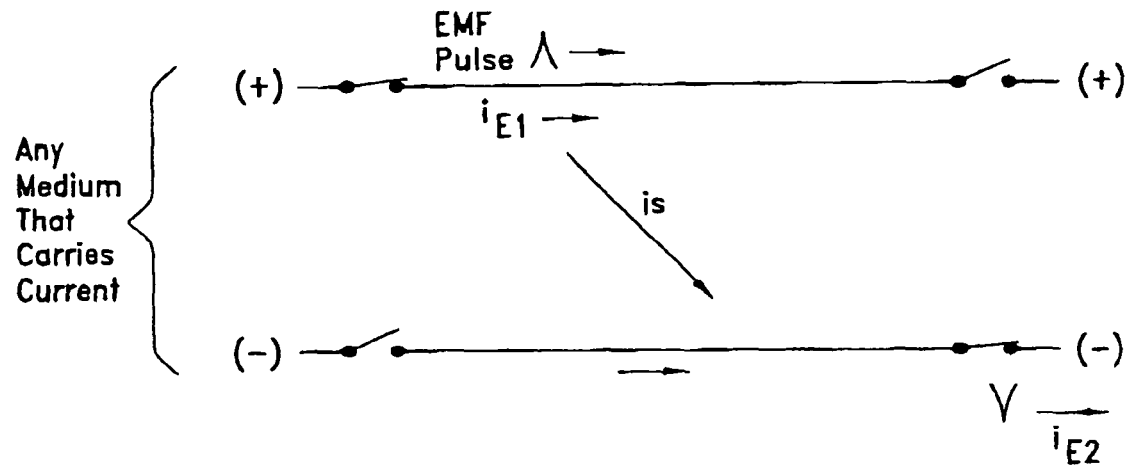
FIGS. 1A and 1B are schematic diagrams illustrating the manner in which a multidirectional current is generated according to the principles of the invention.
Figure 1B:
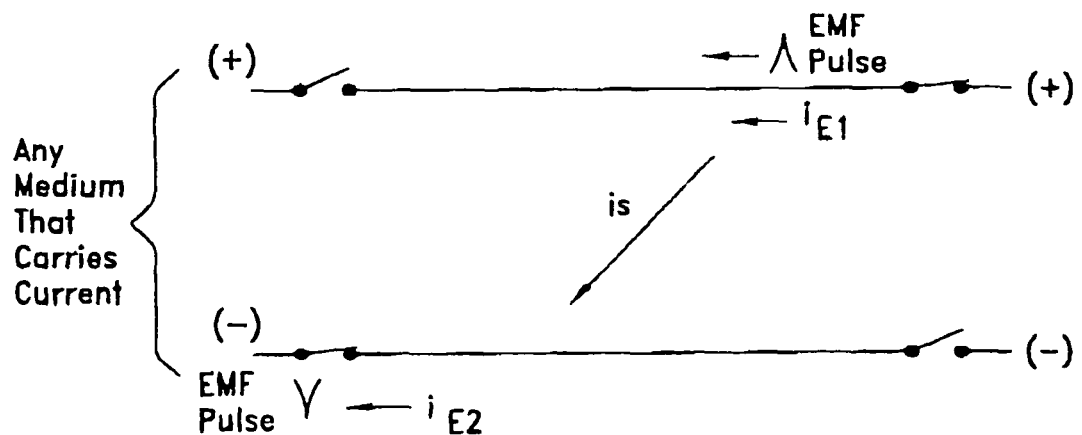
Figure 4:
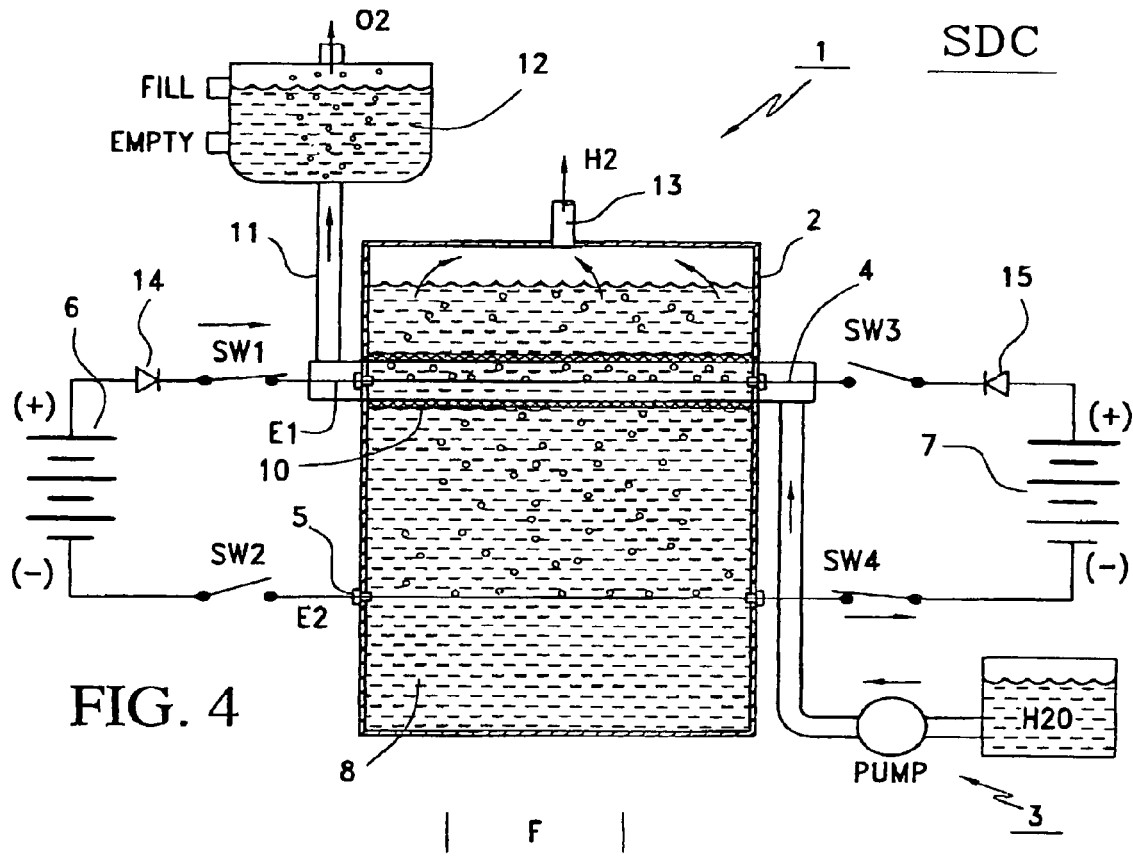
FIG. 4 is a schematic diagram showing the construction of a water electrolysis system that includes an electrolysis cell of the type illustrated in FIGS. 1A, 1B, and 3.

FIG. 4 illustrates an apparatus 1 which utilizes the principles of the invention to generate hydrogen and oxygen according to a first preferred embodiment of the invention. The apparatus 1 includes a tank 2, water supply 3, two electrical conductors 4, 5 which form electrodes corresponding to electrodes E1 and E2 of FIGS. 1A and 1B for an electrolysis process, two conventional DC current sources 6, 7, and four switches SW1-SW4.

The water 8 in this example may include a catalyst such as KOH, as is conventional, although the increased efficiency of the electrolysis process of the invention makes it possible to use ordinary tap water or water from rivers and lakes without adding additional catalysts.

When switches SW1 and SW4 are closed and switches SW2 and SW3 are open, current flows from the positive electrode of power source 6 through switch SW1 to conductor 4, and then is carried by ions in the water 8 to conductor 5, switch SW4, and the negative electrode of power source 7. On the other hand, when switches SW2 and SW3 are closed and switches SW1 and SW4 are open, current flows from the positive electrode of source 7 through switch SW3 into conductor 4, and then is carried by ions in the water to conductor 5, through switch SW2, to the negative terminal of power source 6.

It will be appreciated that there may be a delay between opening of switch pairs SW1, SW4 and closure of switch pairs SW2, SW3, although simultaneous switching is preferred. In addition, the power sources and switching circuitry is not limited to the illustrated batteries and switches, but rather may include any power sources and switching circuitry capable of effecting reversal of currents within the individual electrodes, including solid state switching circuitry and rectified AC power sources. The illustrated diodes 14 and 15 are not essential, and may be omitted or replaced by appropriate voltage regulation, filtering, or other circuit elements.

The ionic current passing through the water from conductor 4 to conductor 5 causes disassociation of hydrogen from oxygen in the water according to the well-known process of electrolysis optionally, the oxygen ($O_2$) produced in the process may be trapped by a membrane 10 encircling conductor 4 for collection through an outlet 11 and storage tank 12, while hydrogen ($H_2$) is collected via an outlet 13.

Variations in the direction of current passing through the water subjects the individual water molecules to shearing as well as tensile forces that expedite disassociation. In addition, different types of microorganisms are known to be sensitive to specific frequencies of electrical current, and therefore switching of the applied conventional currents at an appropriate frequency can have the effect of purifying the water remaining in the tank.

Figure 2:
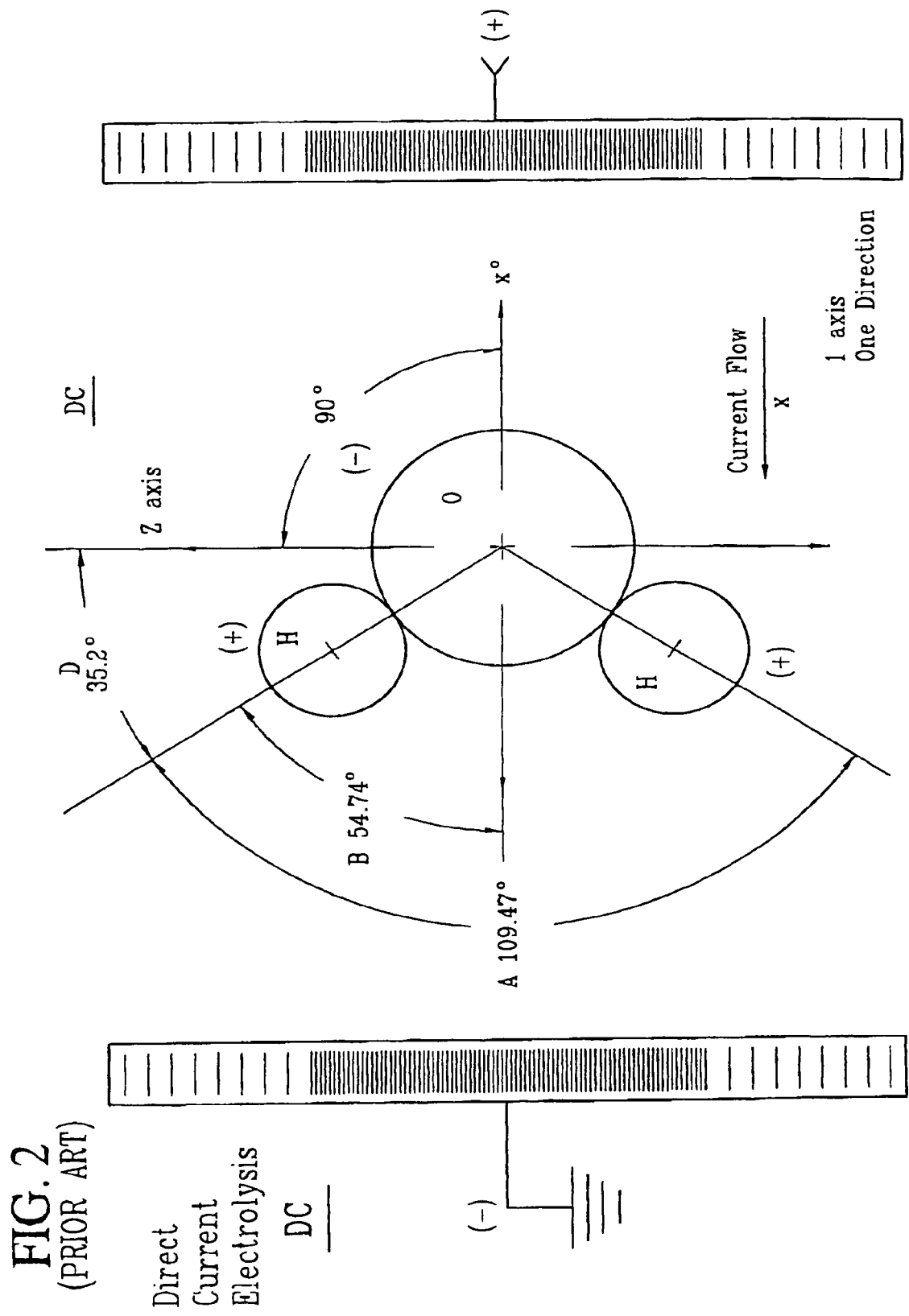
FIG. 2 is a schematic diagram of a conventional electrolysis cell.
Figure 5:
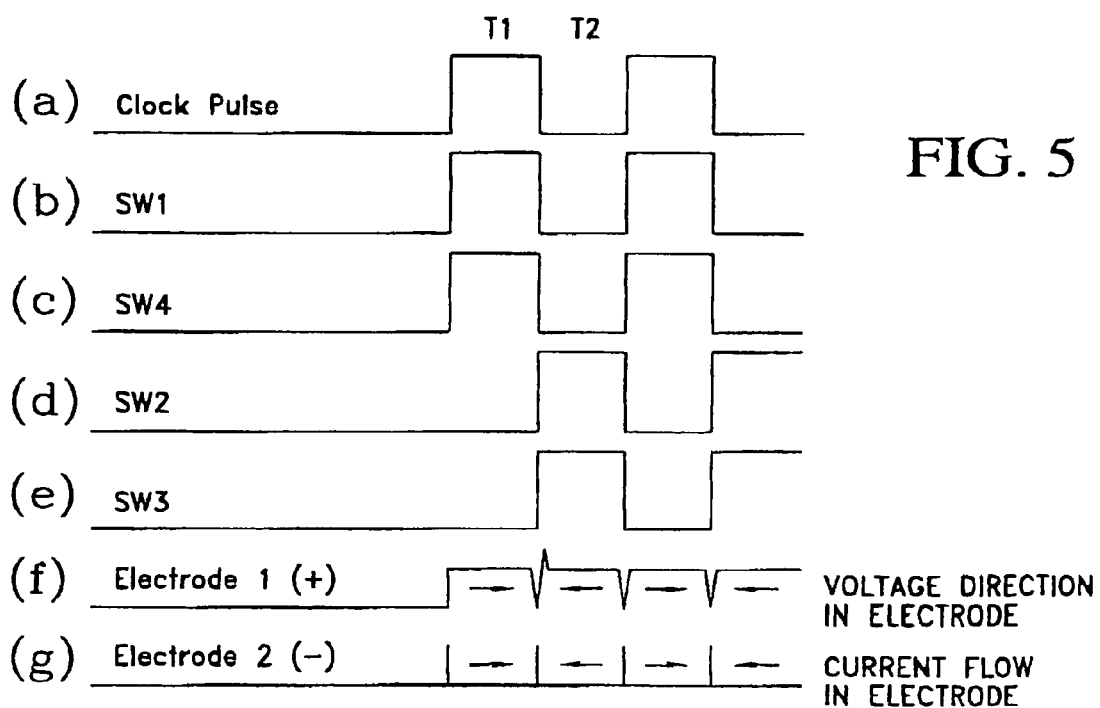
FIG. 5 is a timing diagram for the electrolysis system of FIG. 4.

FIG. 5 shows the electrical currents present at various places in the apparatus of FIG. 4. Timing of the switches may be controlled by a clock pulse illustrated in FIG. 4(a). FIGS. 4(b) to 4(e) show the currents through switches SW1-SW4, respectively, while FIGS. 2(f) and 2(g) show the respective voltages at terminals E1 and E2 between switches SW1, SW4 and conductors 4, 5.

Figure 6:
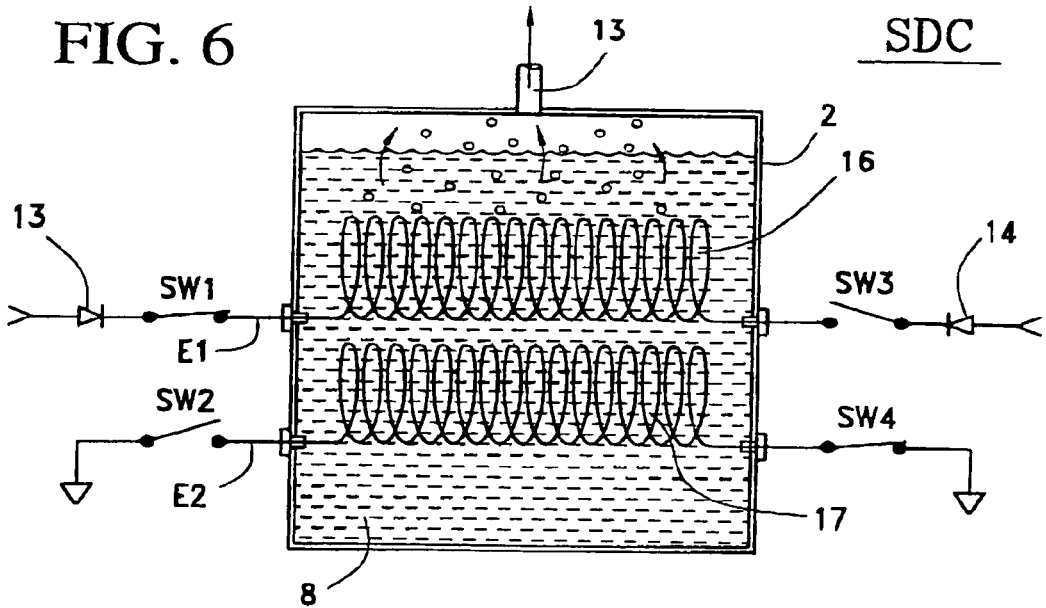

FIG. 6 shows a variation of the electrolytic hydrogen generator of FIG. 4, in which the electrodes E1 and E2 are in the form of coils 16, 17. According to the well-known right hand rule, a magnetic field is generated in the coils 16, 17 having a direction corresponding to the direction of current input to the coils. These fields shift position as they follow the incoming and reversing currents, creating a magnetic vortex that further accelerates disassociation of the water molecules. As illustrated in FIG. 6, only hydrogen ($H_2$) is collected, although of course oxygen may also be collected as necessary, for example by "bagging" one of both of the electrodes 16, 17 in a membrane 10, in the manner illustrated in FIG. 4, or the electrodes may otherwise be separated by a porous barrier to prevent arcing and trap products of the anodic reaction. Alternatively, the coils 16', 17' may be coaxially arranged, as illustrated in FIG. 7, so that the net magnetic fields will cancel out, even though the instantaneous magnetic fields will still change.

Figure 7:
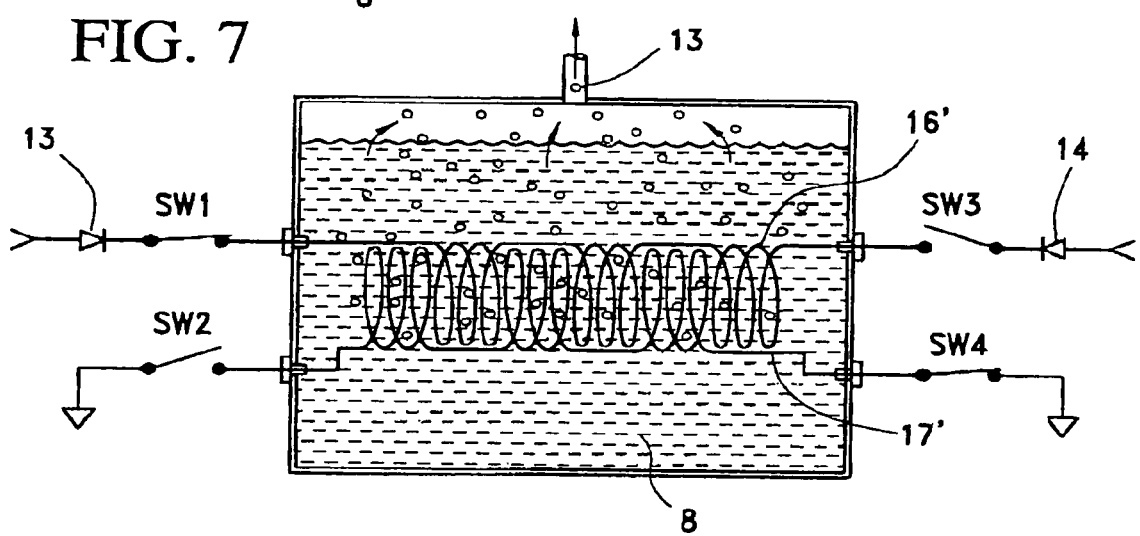

It will be appreciated that the magnetic fields generated in the embodiments of FIGS. 6 and 7 have advantages apart from the advantages resulting from reversal of the currents in the electrodes, and therefore the apparatus of this is embodiment is not intended to be limited to multi-directional current generation. Instead, it is within the scope of the invention to apply DC, pulsed DC, reversing polarity, and AC voltages, as well as various multi-directional currents, to the coiled electrodes, and to cause the magnetic fields to synchronously or non-synchronously reverse polarities and/or directions, with the fields either reinforcing each other or cancelling out.

The magnetic fields generated by the coaxial coil electrolytic cell apparatus of FIG. 7 are capable of generating a substantial gas flow even when the medium between the coils 16', 17' is ordinary tap or distilled water, at coil spacings of between 0.005 and 0.500 inches, and preferably between 0.050 and 0.200 inches. When a catalyst such as potassium hydroxide (KOH) is added to the water, the spacing between the two coils 16', 17' may be between 0.032 and 6.000 inches, with the preferred spacing still being between 0.050 and 0.200 inches. In addition, the gap or spacing between adjacent coils 16', 17' of each electrode may be between 0.001 and 0.500 inches, with a preferred gap of 0.032 to 0.100 inches.

As in the non-coiled embodiments, the electrolytic reaction rate may be increased still further by applying light to the apparatus, so that the energy of the photons adds to the energy supplied by the electric fields between the electrodes and the magnetic fields within the electrodes. Either or both of the electrodes may be enclosed within a membrane bag, sack, or tubing, as also discussed above, and currents and/or fields may further be arranged to kill microorganisms.

Figure 3:
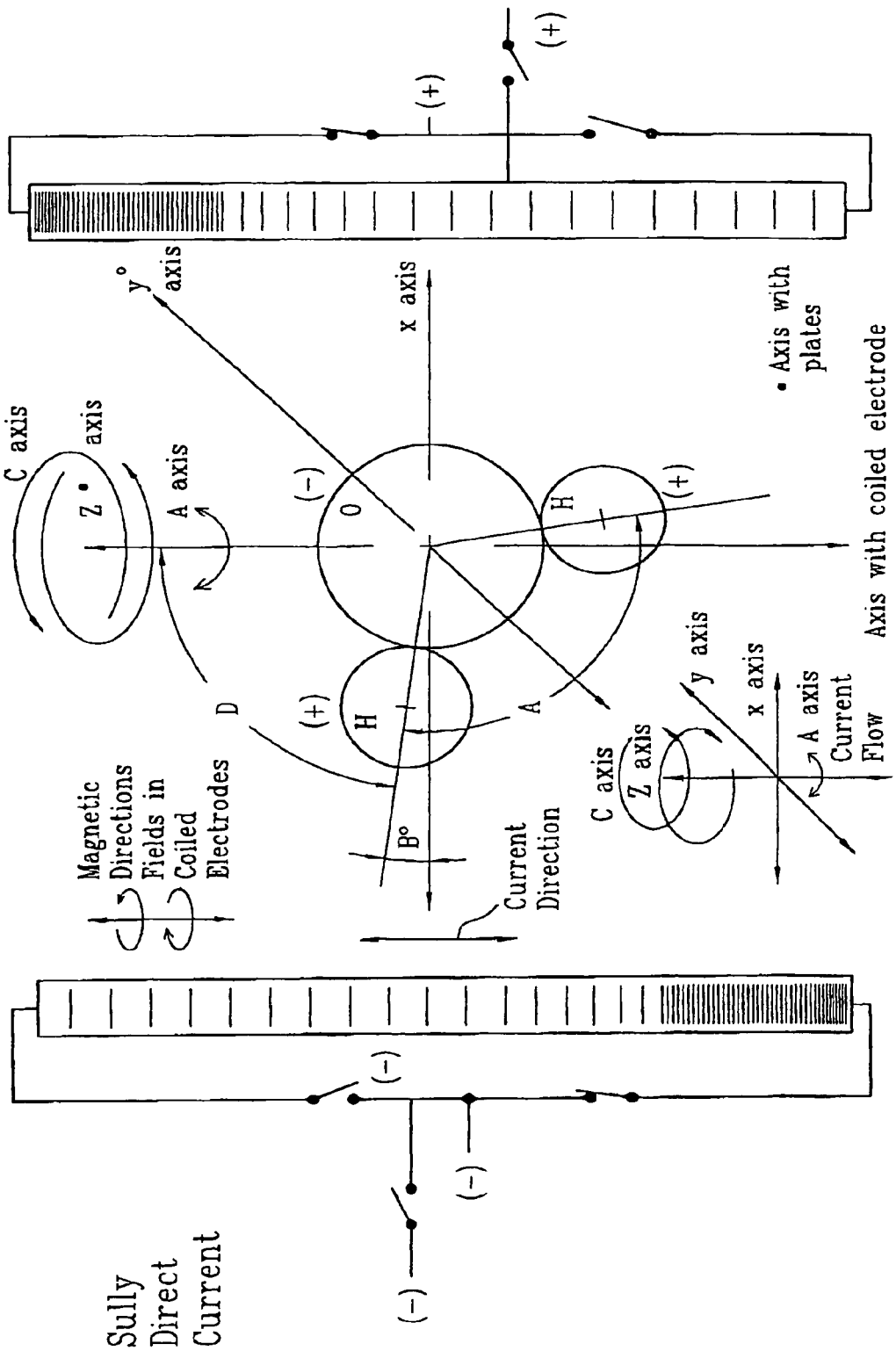
FIG. 3 is a schematic diagram showing the operation of an electrolysis cell constructed in accordance with the principles of the present invention.
Figure 8:
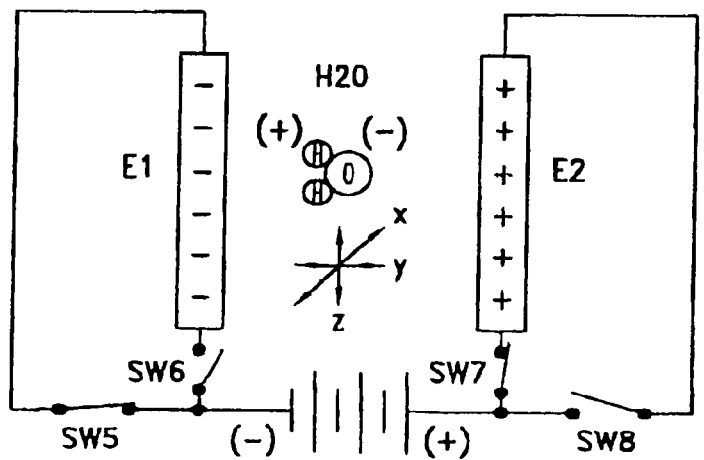

FIG. 8 illustrates a variation of the switching system illustrated in FIG. 4, in which a single battery or cell is used to supply electricity to the two electrodes E1 and E2. In this system, closed switches SW5 and SW7 cause current in electrodes E1 and E2 to flow in a first direction when switches SW6 and SW8 are open, while closed switches SW6 and SW8 and correspondingly open switches SW5 and SW7 cause current to reverse and flow in an opposite direction. The reversal affects the shearing and tensile force separation of the water molecules in the manner earlier described with respect to FIG. 3.

FIG. 9 illustrates a variation of the system of FIG. 7 in which AC current is applied to the at least one of the electrodes, and the direction of the AC current is reversed by alternately opening and closing the switches SW1, SW4 and SW2, SW3.

FIG. 10 illustrates a lighting system in which the electrolyte is replaced by a material 20 that emits light when excited by a reversing current generated by alternately opening and closing the switches SW1, SW4 and SW2, SW3.

Those skilled in the art will appreciate that the multidirectional current generating apparatus of FIGS. 4-10 may also be connected together in various combinations. For example, FIG. 11 illustrates two electrolytic cells 22 and 23, each corresponding to the cell illustrated in FIG. 8, connected in parallel. FIG. 12 illustrates the same two electrolytic cells connected in series. In each case the current is reversed by alternately opening and closing the switches SW1, SW4 and SW2, SW3.

Figure 13:
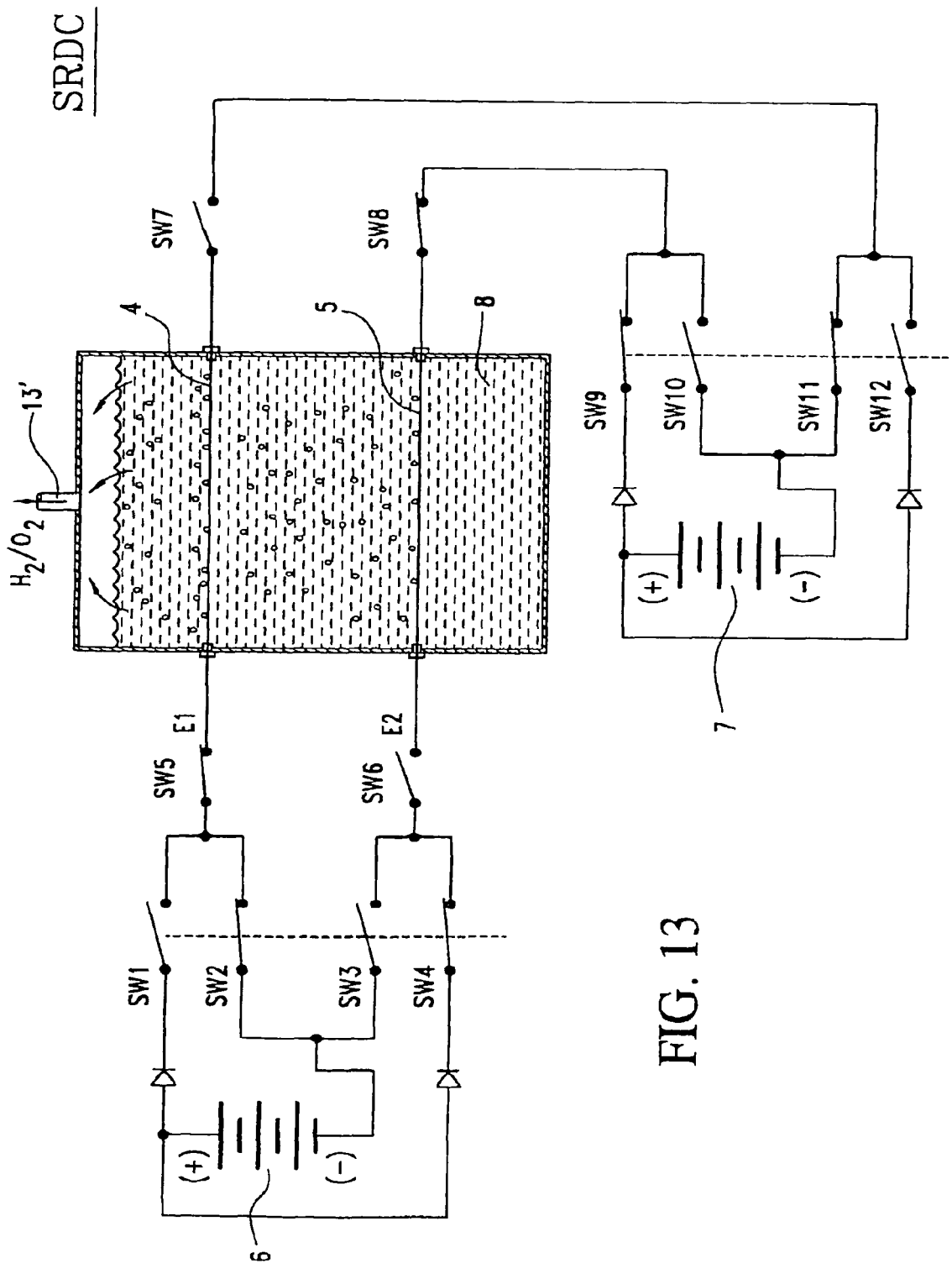

FIG. 13 illustrates an apparatus corresponding to that of FIG. 4, but with additional polarity reversal of the two electrodes 4, 5. In the apparatus of FIG. 13, switches SW5 to SW8 effect current reversal within the electrodes to generate a multidirectional current in the current carrying medium 8, illustrated as water, while switches SW1 to SW4 reverse the polarity of electrode 4 and switches SW9 to SW12 reverse the polarity of electrode 5. A corresponding timing diagram is illustrated in FIGS. 14(a) to 14(o).

Figure 15:
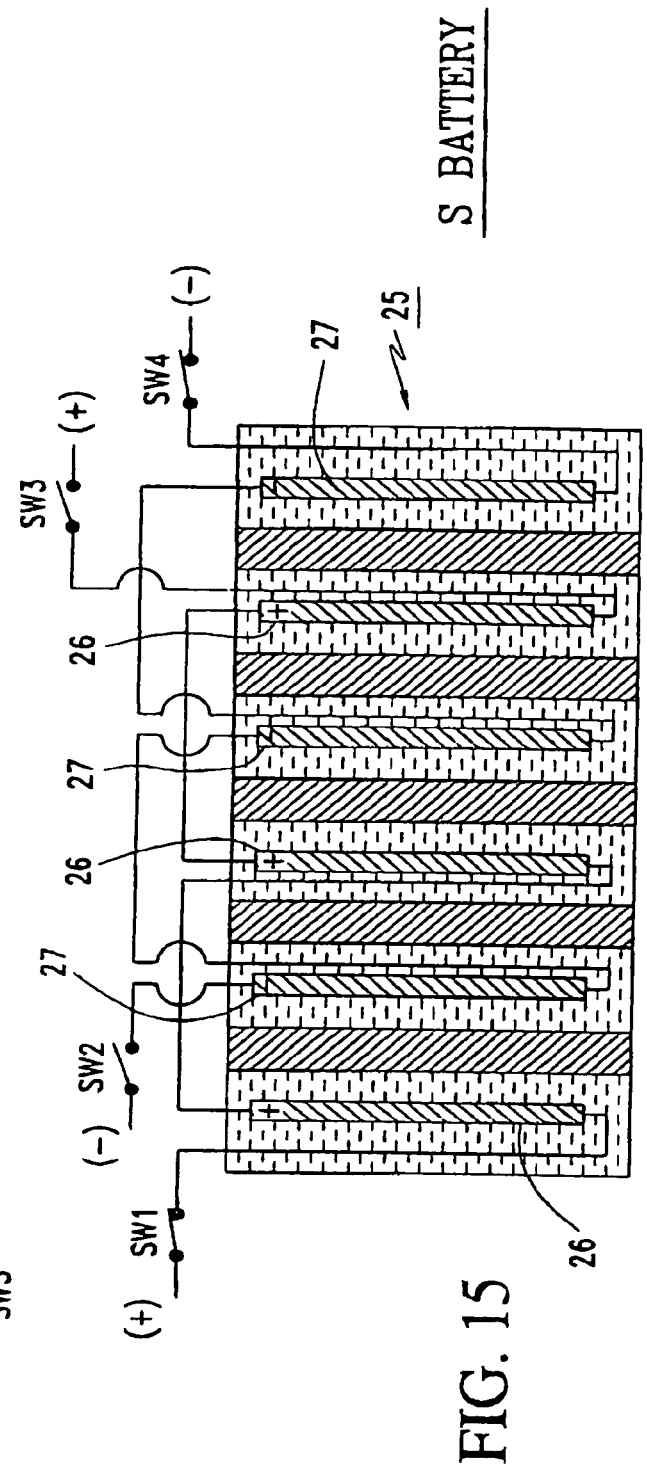
FIGS. 15-17 are schematic diagrams of various applications of the principles of the invention to the charging of batteries.

FIG. 15 shows a charging circuit for an electrolytic battery 25, which may be a nickel metal hydride battery of the type described in U.S. Pat. No. 6,413,670, but which includes a current reversal circuit of the type illustrated in FIG. 4 for reversing the direction of currents in the positive electrodes 26 and the negative electrodes 27. The illustrated current reversal prevents asymmetric accumulation of ions on the electrodes, and therefore reduces wear caused by excessive heating, while the multi-directional current in the electrolyte reduces buildup of electrolytic reactants on the terminals. In addition, in the case of a nickel metal hydride battery, the current reversal facilitates absorption of hydrogen by the nickel material.

Figure 16:
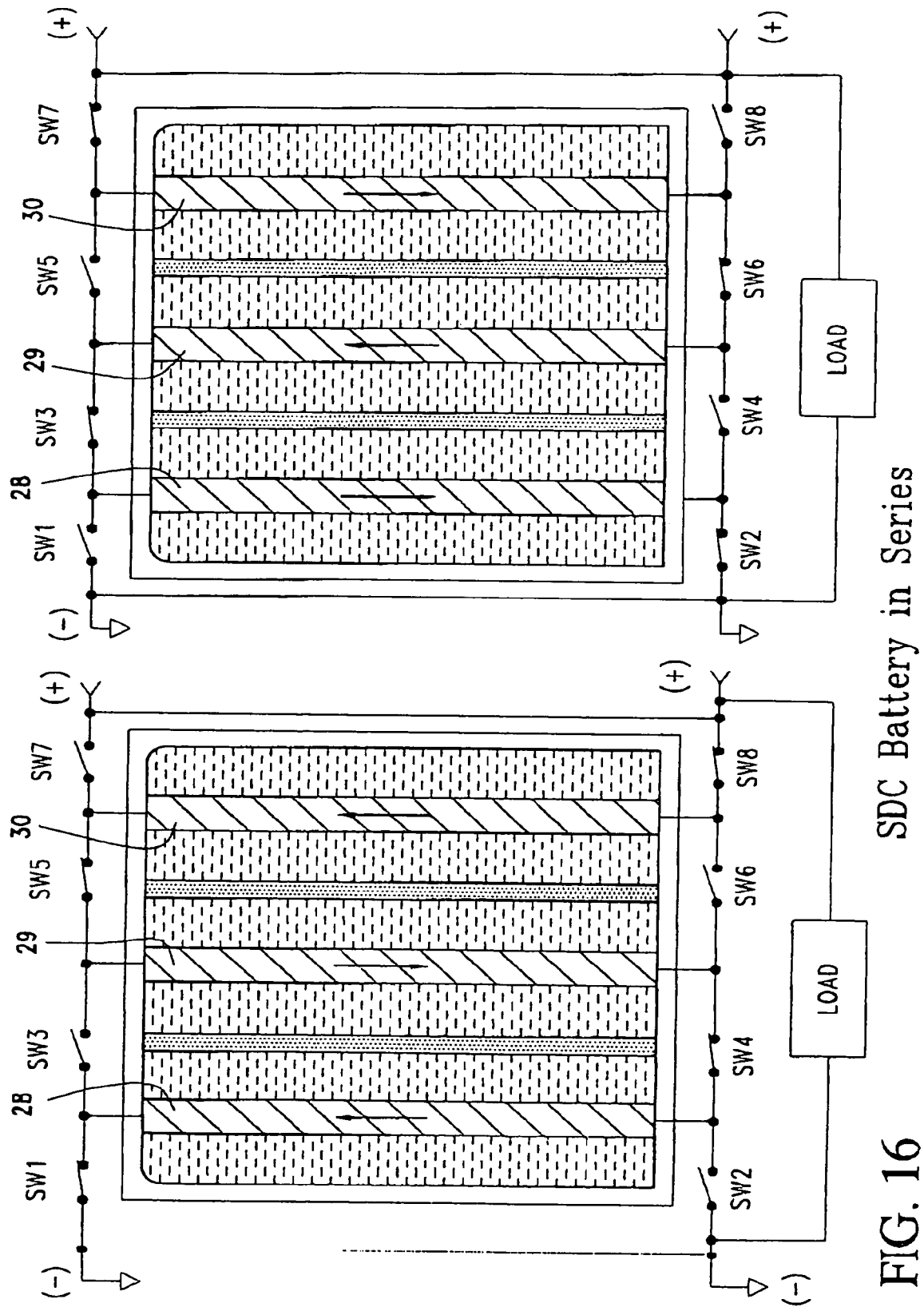

FIG. 16 illustrates an alternate switching circuit for batteries of the type illustrated in FIG. 15, with the electrodes 28-30 connected in series.

Figure 17:
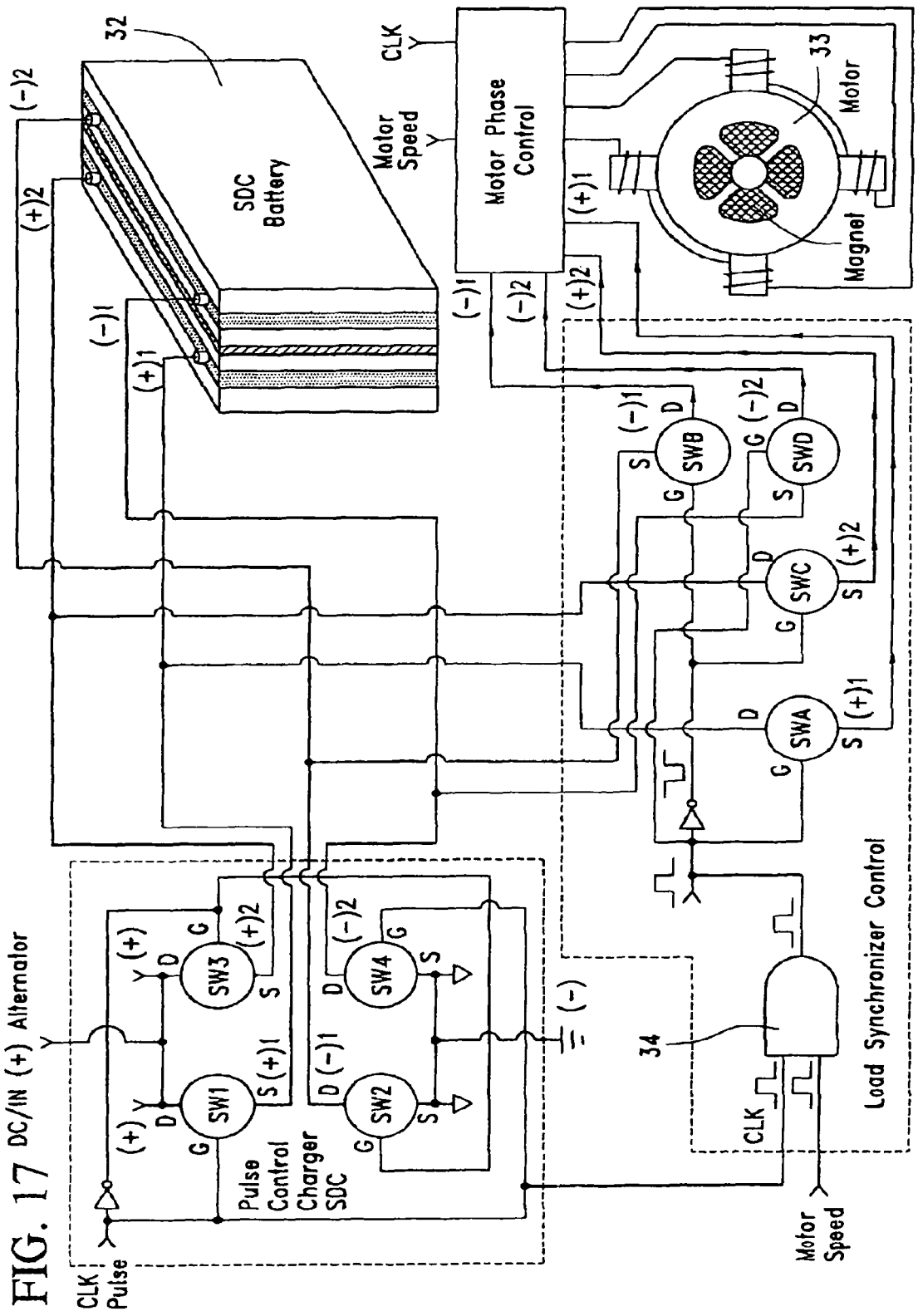
Figure 18:
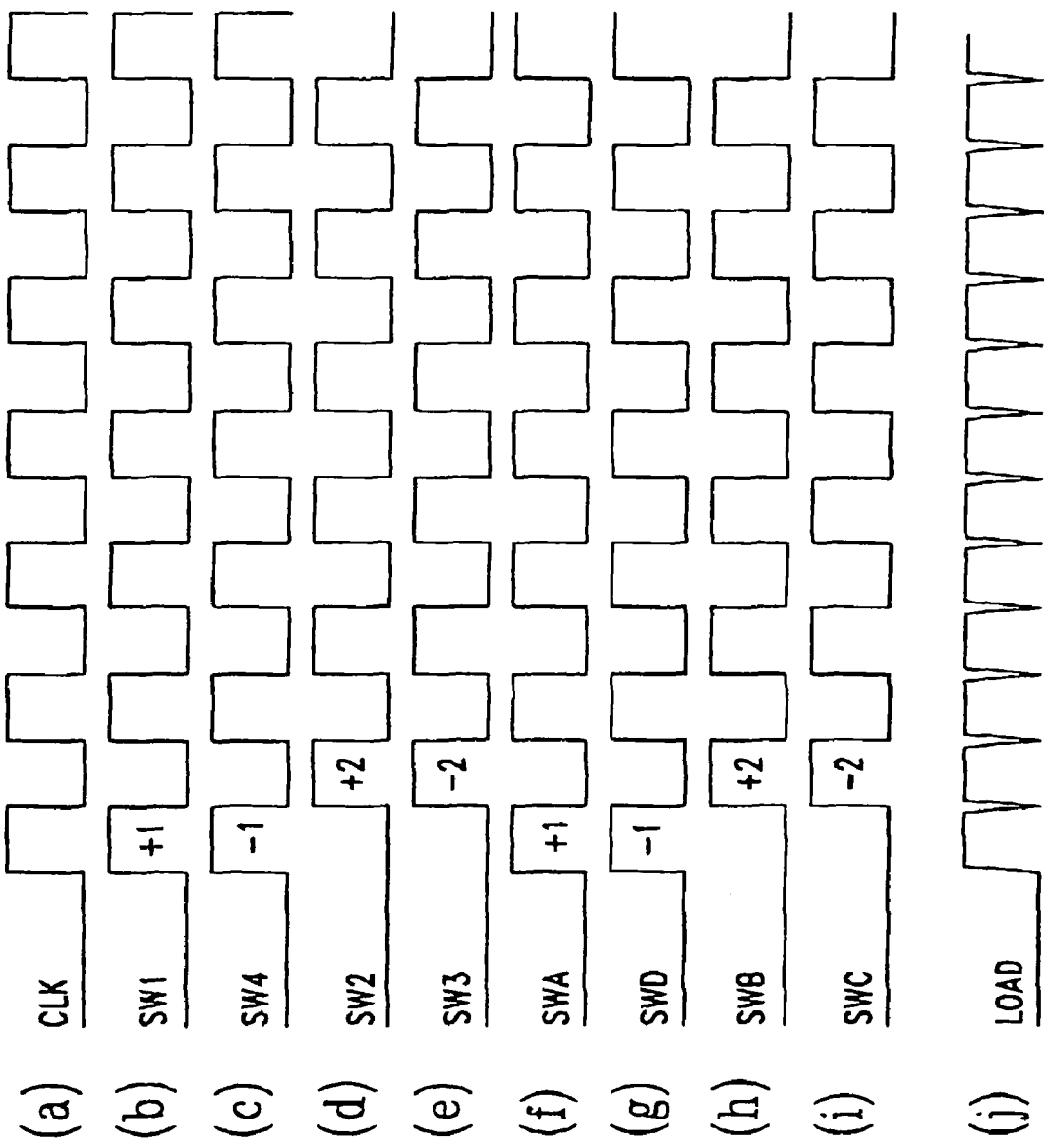
FIG. 18 is a timing diagram for the battery charge/discharge circuit of FIG. 17.

Operation of the battery can be further improved by adding a current reversing discharge circuit to the current reversing charging circuit to prevent excess wear due to asymmetric discharge currents. As illustrated in FIG. 17, discharge of a battery 32 is synchronized to the phase of a motor 33 by means of a synchronizer control 34 and motor commutating switches SWA to SWD. In this embodiment, switches SW1 to SW4 operate in the same manner as the corresponding switches of the water electrolysis system or hydrogen generator illustrated in FIG. 4. A timing diagram for the synchronized charge and discharge of the battery of FIG. 17 is included in FIGS. 18(a) to 18(j).

It will be appreciated that the principles of the invention may be applied to a variety of different types of batteries, including hydrogen batteries as well as the illustrated nickel metal hydride battery, and the invention is not to be limited to a particular type of battery.

Figure 19:
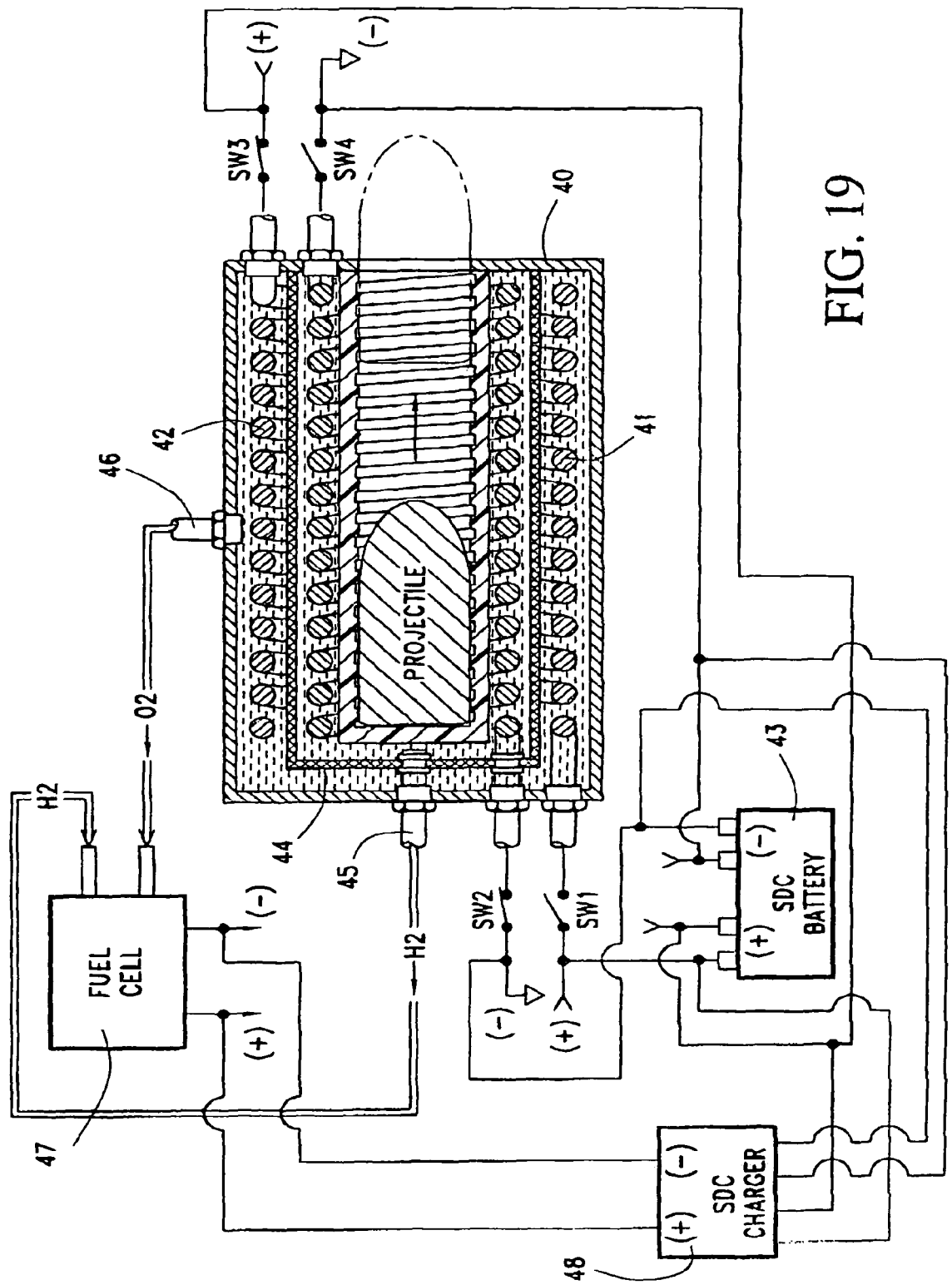
FIGS. 19 and 20 are schematic diagrams of various applications of the principles of the invention to electromagnetic devices.
Figure 20:
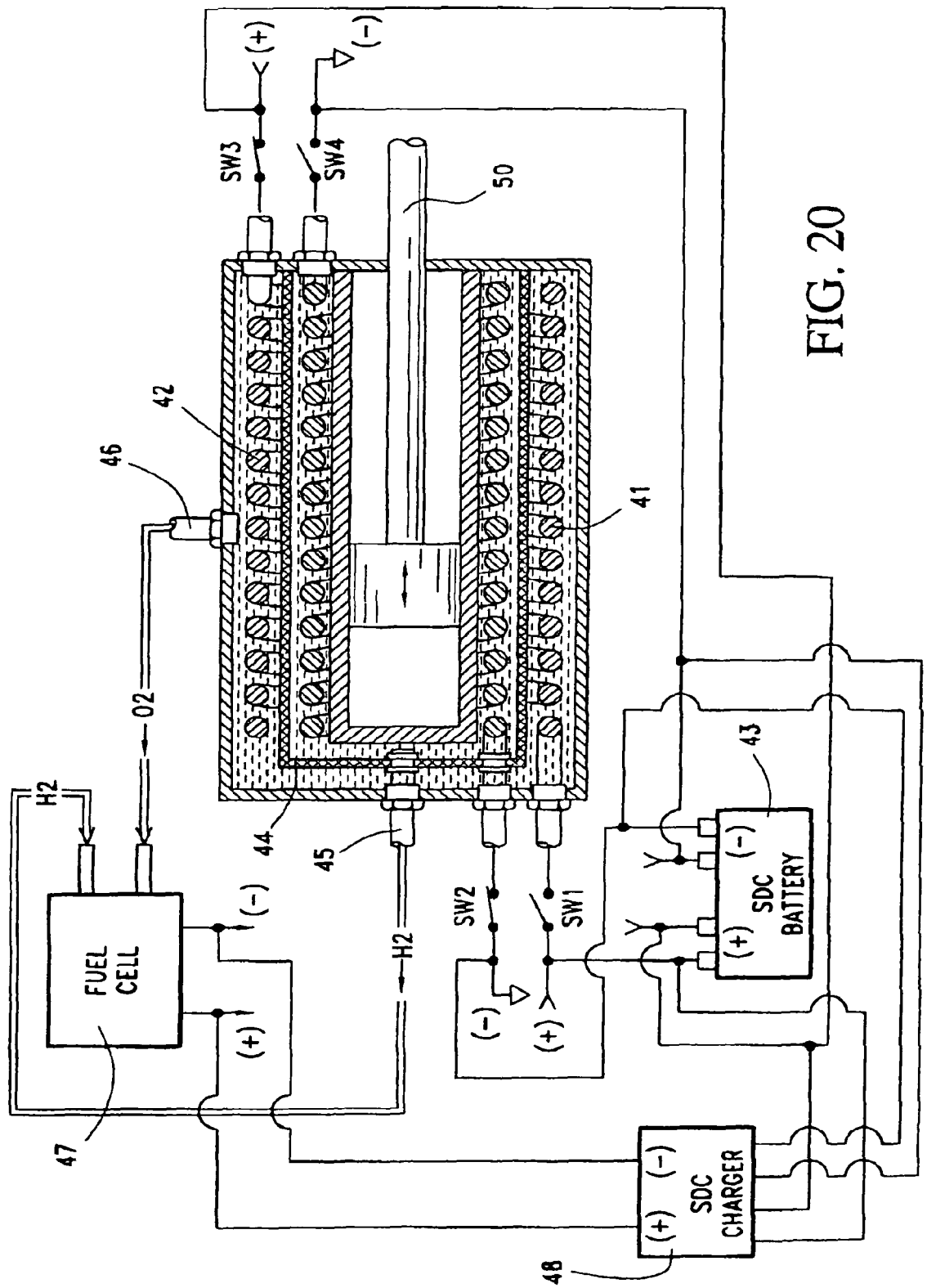

FIGS. 19 and 20 illustrate application of the principles of the invention to an electromagnetic device such as an electromagnetic projectile launcher 40 (FIG. 19) or a piston driver 50 (FIG. 20). In each of these devices, two electrodes 41 and 42 are arranged coaxially and oppositely wound to generate a magnetic flux in a common direction. The reversing DC currents are supplied to the coils by a battery 43 of the type illustrated in FIG. 15 through switches SW1 to SW4, with oxygen and hydrogen being generated by electrolysis and separated by a membrane 44. The oxygen ($O_2$) and hydrogen ($H_2$) are discharged via respective outlets 45 and 46 to a fuel cell 47 which generates electricity for use in charging the battery 43 through charging circuit 48 when the devices are in a standby state, and for driving the projectile (PROJECTILE) shown in FIG. 19 or piston (50) shown in FIG. 20 when the devices are active.

Figure 21:
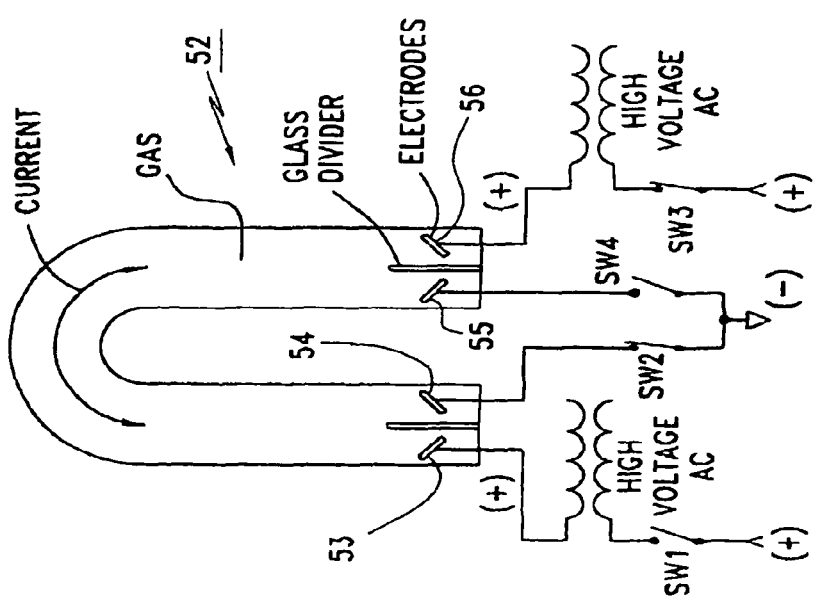
FIG. 21 is a schematic diagram of a cold cathode light system that utilizes the principles of the invention.

FIG. 21 shows details of a cold cathode light 52 having electrodes 53-56 alternately supplied with a high voltage AC current through switches SW1 to SW4. In this application, the current in the lighting medium (GAS) switches direction because it alternately flows between electrode pairs 53, 55 and 54, 56 rather than because of current reversals within the electrodes.

Figure 22:
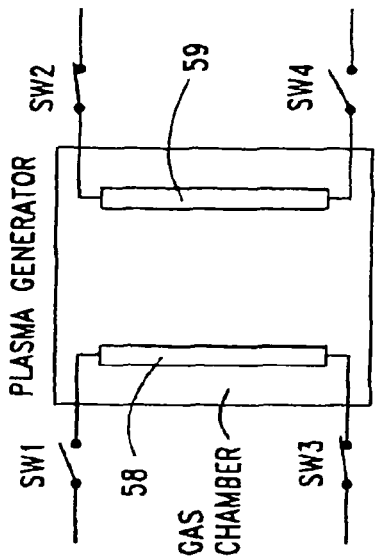
FIG. 22 is a schematic diagram of a plasma generator that utilizes the principles of the invention.

FIG. 22 shows a plasma generator having a switching circuit identical to that shown in FIG. 4, but in which the current carrying medium is a gas, the current reversals in the electrodes 58 and 59 generating a multidirectional current in the gas that increases the rate and uniformity of plasma generation.

Figure 24:
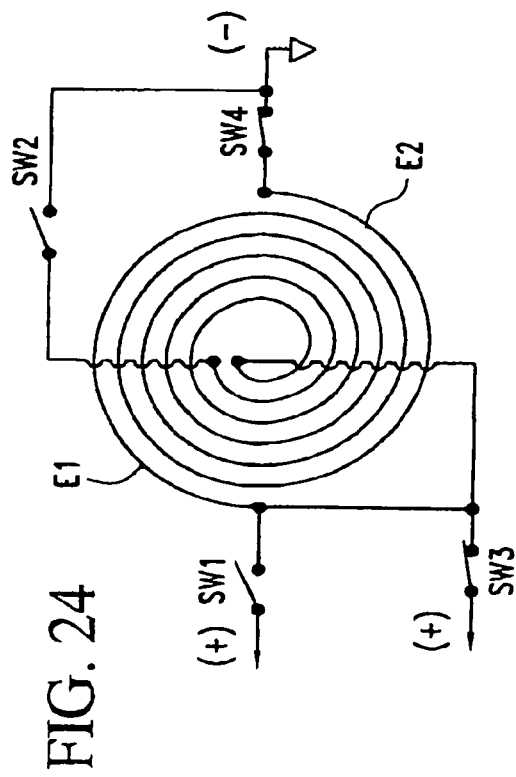
FIG. 24, which appears with FIG. 15, and FIG. 25 are schematic diagrams of jelly roll versions of the electrolysis cells and/or batteries of the preferred embodiments.
Figure 23:
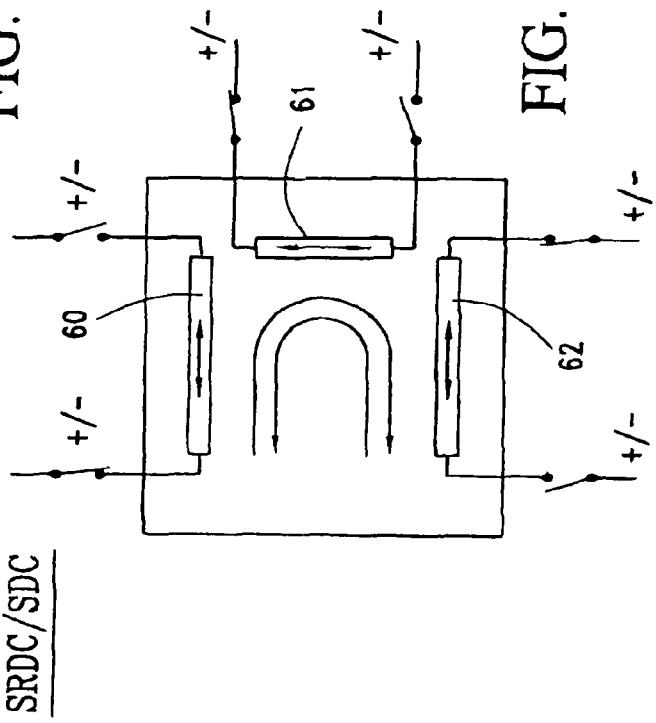
FIG. 23 is a schematic diagram illustrating application of the invention to a three electrode device.
Figures 25, 26:
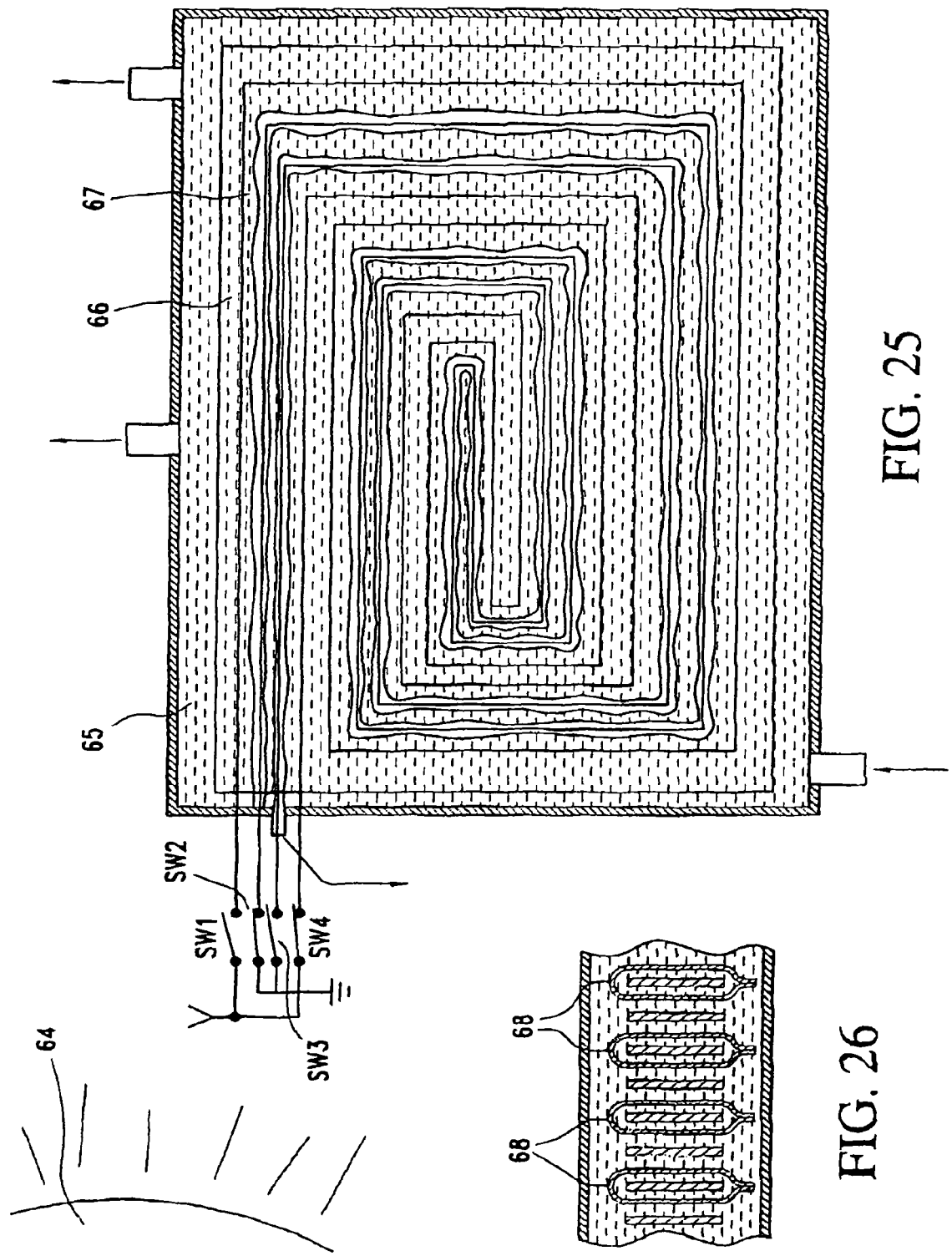
FIG. 26 is a schematic diagram of a multiple electrode electrolysis cell.
Figure 27:
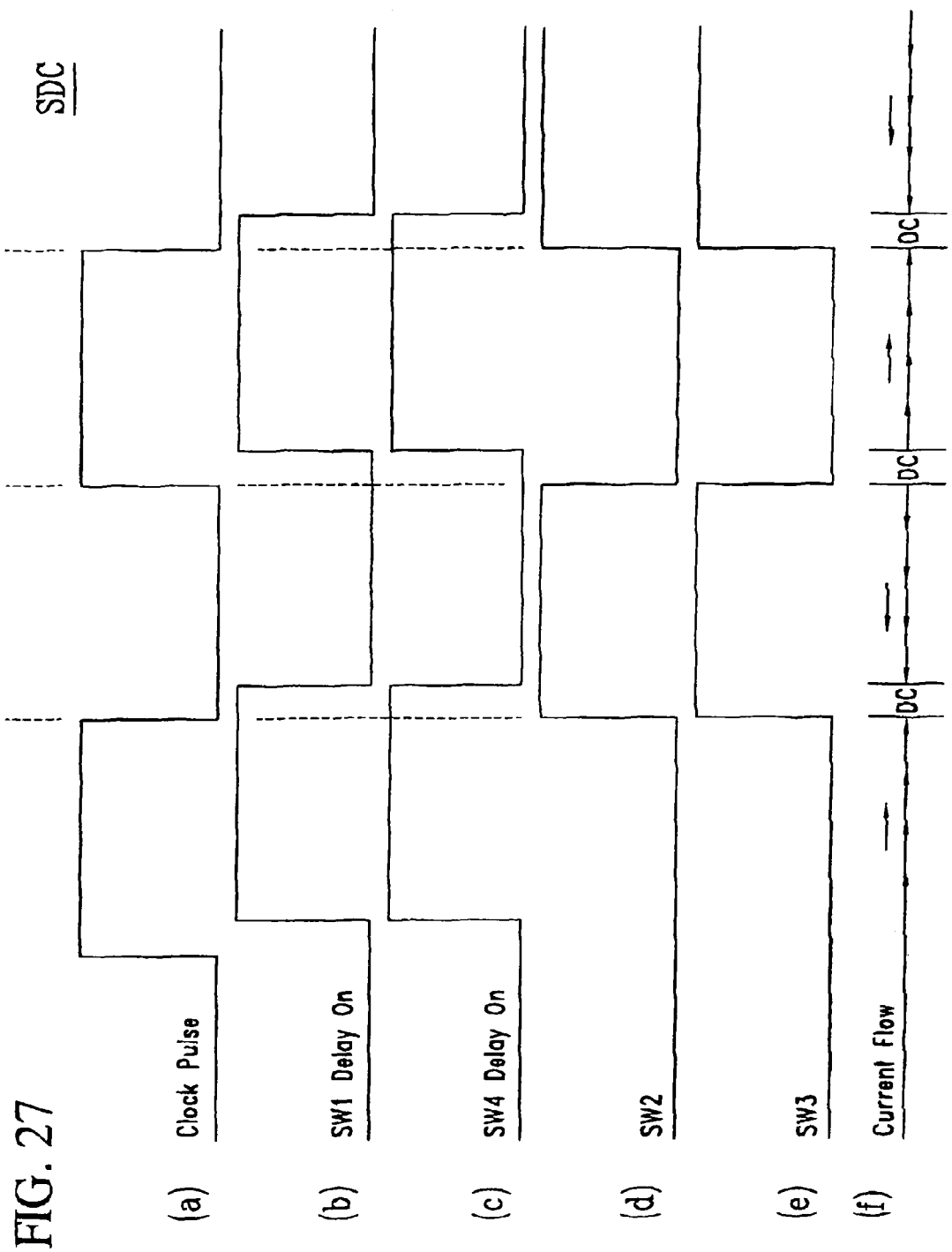
FIG. 27 is an alternative timing diagram for the switching circuit illustrated in FIG. 4.

In addition to the numerous different applications described above, the configuration and number of the electrodes may be varied in a variety of ways without departing from the scope of the invention. For example, more than two electrodes may be included, such as the three electrodes 60-62 shown in FIG. 23, or the electrodes may be interleaved as illustrated in FIGS. 24 and 25. FIG. 25 shows the additional feature of an external light source 64 for further increasing the rate of gas production, as described in US Patent Published Patent Application No. 2002/0060161 (entitled Photo-Assisted Electrolysis) in an electrolysis cell 65 that can be used as part of, or to enhance, a regenerative solar electricity generating system, and that uses planar coiled electrodes 66 and 67 arranged in a jelly roll configuration. FIG. 26 illustrates an alternate gas separation system in a multiple electrode electrolysis cell corresponding to the one illustrated in the above cited copending patent application, and that uses multiple membranes 68 housing or bagging alternate electrodes.

The principles of the invention may also be applied to various capacitive systems, as illustrated in FIGS. 29-37, by using a material or structure 70 that permits passage of ions as a dielectric separator between the electrodes E1, E2 of the capacitor. For example, as illustrated in FIGS. 29 and 30, the direction of currents between the two electrodes E1, E2 of a single capacitor, or the respective electrodes E1, E2 of multiple capacitors connected in series (FIG. 29) or parallel (FIG. 30), may be reversed using four or more switches SW1-SW8 in the same manner as described above in connection with FIG. 4. By symmetrically charging and discharging the capacitors, asymmetric heat build-up in the electrodes is prevented, improving performance and extending the life of the capacitors.

The capacitors to which the principles of the invention are applied may take, of course, a variety of forms, and are not limited to a particular electrode geometric or specific electrode or dielectric materials. FIG. 31, for example, shows a jelly roll capacitor configuration similar to the jelly roll configuration of the electrodes in the electrolytic cell of FIG. 25.

As especially advantageous application of the principles of the invention to capacitive systems is the thrust module illustrated in FIGS. 32 and 33, which improves upon the thrust module described in U.S. Pat. No. 6,317,310 by varying the direction of currents applied to high voltage electrode plate 72, thereby enabling the thrust direction to be varied. In this configuration, the negative electrode 74 has switch terminals at each end, in a manner similar to the other embodiments of the invention, but the positive electrodes have additional switch terminals SW1-SW8 so as to enable the direction of current in the dielectric 76 to not only be reversed, but also to change angular position and thereby the thrust angle, depending on which pairs of switches are operated.

Figure 34:
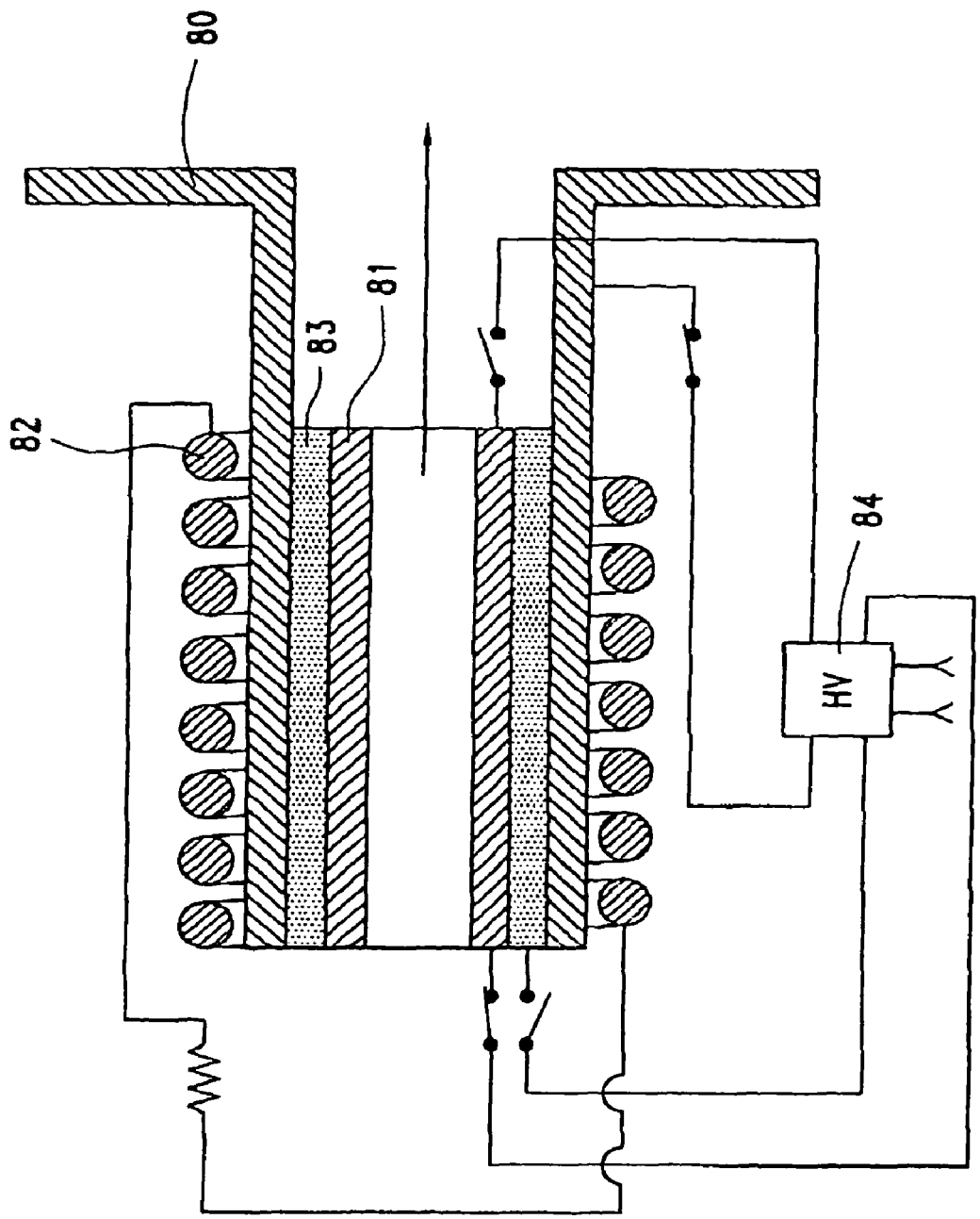
FIG. 34 is a cross-sectional view of a capacitive thrust module with an EMF capture coil.

FIG. 34 illustrates a variation of the thrust module of FIGS. 32 and 33, in which current is supplied by a high voltage source 84 to electrodes 80 and 81, which coaxially surround dielectric material 83, through current-direction reversing switches SW1-SW4, and the resulting EMF pulses in electrodes 80 and 81 are captured by a coil 85 to produce a voltage when the current changes direction, thereby generating magnetic fields to create a thrust force.

Figure 35:
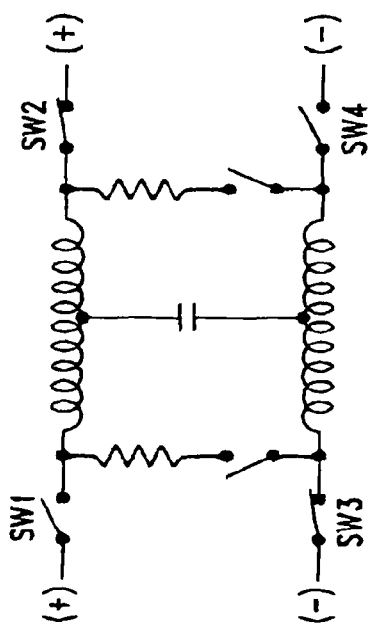
FIG. 35 is a schematic diagram of an RLC circuit that charges when current flow is changed according to the principles of the invention.
Figure 36:
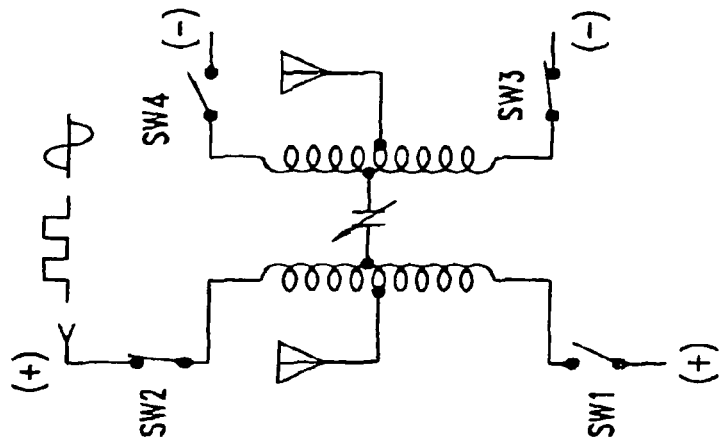
FIG. 36 is a schematic diagram of a transmitter circuit with a tuned capacitor in which the current change amplifies the signal on both the plus and minus side of the circuit according to the principles of the invention.
Figure 37:
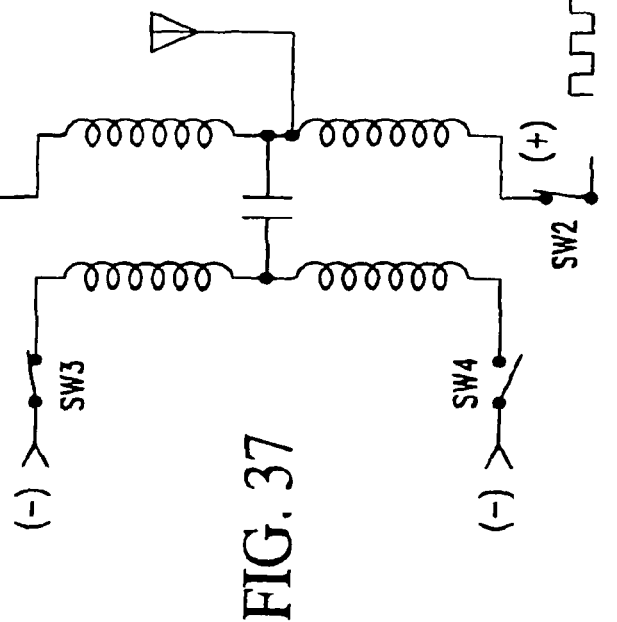
FIG. 37 is a schematic diagram of a capacitor circuit in which the capacitance is controlled by currents in the electrolyte.

Capacitors or capacitor circuits of the type illustrated in FIGS. 29-33 may also be used in a variety of other capacitor circuits, such as the ones illustrated in FIGS. 35-37. FIG. 35 shows an RLC circuit that charges when the direction of current is changed using switches SW1 and SW4, while FIG. 36 shows a tuner circuit for a transmitter in which the current change amplifies the transmitted signal on both the plus and minus sides of the circuit, and FIG. 37 shows an alternative capacitor construction and circuit in which the capacitance is controlled by the adjusted electrolyte 90 in which the capacitor electrodes 91, 92 are immersed.

Figure 28:
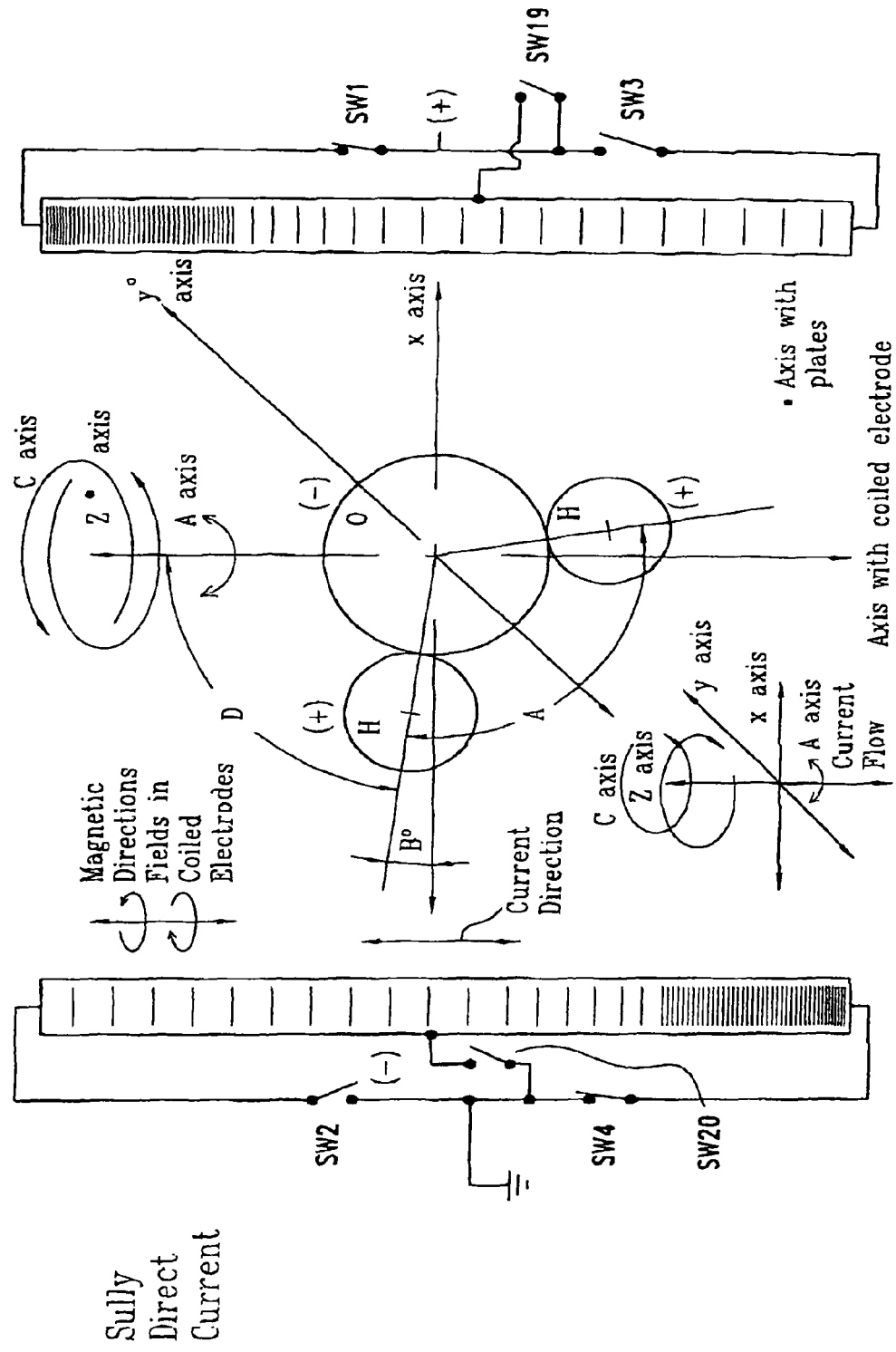
FIG. 28 shows a variation of the arrangement schematically illustrated in FIGS. 1A and 1B, with additional switches and center taps for controlling the electromagnetic pulses in each electrode.

Those skilled in the art will appreciate that in any of the above-described embodiments and implementations of the invention, both the manner in which the current is caused to alternate direction in the electrodes, and the timing and magnitude of the EMF pulses, can be varied according to the principles of the invention. For example, FIGS. 27(a)-27(f) are timing diagrams of a variation of the preferred switching system in which opening and closing of switches SW1 and SW4 is delayed relative to closing and opening of switches SW2 and SW3. On the other hand, FIG. 28 illustrates a variation of the apparatus illustrated in FIG. 3, in which center taps and switches SW19 and SW20 are added to enable manipulation or softening of the EMF pulses in the electrodes.

In addition to the illustrated applications, other potential applications of the principles of the invention are as follows:

The electrolytic cell illustrated in FIG. 4 or an analogous switched semiconductor device could also be used as a type of computing device in which sensors monitor the direction of current flow. Instead of using Boolean logic, the computer would use the current flow sensors to sense directions, with zero current to 0, and different current directions to +1, +2, +3, and so forth. In addition, the transistors that change the direction of the current may be part of a ladder logic equation and for setting the timing and logic expression, for example by performing a flip flop function timed with current flow.

Another possible application is to use the currents to reduce radioactive waste of spent nuclear fuel by attaching the electron orbits of spent fuel in a multi-dimensional oscillating electric field, or a polarity reversing multi-dimensional electric field.

It will be appreciated that one can build an electromagnetic generator that will produce multi-directional currents and corresponding voltages, rather than converting the currents or voltages from another DC or AC voltage. Also, mechanical cam switching can create multi-directional currents and corresponding voltages, and one can similarly build motor that will run on new the voltages.

Finally, yet another possible application of the invention is to enhance dehydration of a porous material using electro-osmosis as described in U.S. Pat. Nos. 6,117,295 and 6,372,109.

Having thus described a preferred embodiment of the invention in sufficient detail to enable those skilled in the art to make and use the invention, it will nevertheless be appreciated that numerous variations and modifications of the illustrated embodiment may be made without departing from the spirit of the invention, and it is intended that the invention not be limited by the above description or accompanying drawings, but that it be defined solely in accordance with the appended claims.

I claim:

1. An electrical energy storage/discharge device, comprising:
   at least two electrodes;
   a current carrying medium between said electrodes;
   at least one power supply;
   circuitry connected between said at least one power supply and two ends of at least one of said electrodes for alternately supplying a current to respective said ends of said at least one of said electrodes in order to cause a cyclically reversing electrical current to flow within said electrode between said ends, wherein:
   (a) cyclical reversal of the electrical current within said at least one of said electrodes causes electromotive force (EMF) pulses to travel along said electrode, and
   (b) said movement of said electromotive force pulses causes a multidirectional electric current flowing between said at least two electrodes to change directions.

2. An electrical energy storage/discharge device as claimed claim 1, wherein electrodes and current carrying medium form a battery.

3. An electrical energy storage/discharge device as claimed claim 2, wherein said battery is a nickel metal hydride battery.

4. An electrical energy storage/discharge device as claimed claim 1, wherein said circuitry includes respective switches connected between a terminal of the power supply and each end of each of said electrodes, and wherein said switches are arranged to be alternately opened and closed.

5. An electrical energy storage/discharge device as claimed claim 4, wherein said switches are selected from the group consisting of electromechanical, solid state, and photonic switches.

6. An electrical energy storage/discharge device as claimed claim 2, further comprising a load connected to said circuitry and synchronized to discharge said battery in step with current switching by said circuitry.

7. An electrical energy storage/discharge device as claimed claim 6, wherein said load is a motor.

8. An electrical energy storage/discharge device as claimed claim 2, further comprising means for collecting hydrogen generated during charging of said battery.

9. An electrical energy storage/discharge device as claimed in claim 1, wherein said electrodes and current carrying medium form a capacitor.

10. An electrical energy storage/discharge device as claimed in claim 1, wherein said electrical energy storage/discharge device comprises at least two pairs of said electrodes and one said current carrying medium between each respective pair of said electrodes to form two batteries.

11. An electrical energy storage/discharge device as claimed in claim 10, wherein said batteries are connected in series.

12. An electrical energy storage/discharge device as claimed in 10, wherein said batteries are connected in parallel.

13. An electrical energy storage/discharge device as claimed in claim 1, wherein said electrical energy storage/discharge device comprises at least two pairs of said electrodes and one said current carrying medium between each respective pair of said electrodes to form two capacitors.

14. An electrical energy storage/discharge device as claimed in claim 13, wherein said capacitors are connected in parallel.

15. An electrical energy storage/discharge device as claimed in claim 13, wherein said capacitors are connected in series.

16. An electrical energy storage/discharge device as claimed in claim 10, wherein said electrical energy storage/discharge device comprises at least two pairs of said electrodes and one said current carrying medium between each respective pair of said electrodes.

17. An electrical energy storage/discharge device as claimed in claim 16, wherein said batteries are connected in series.

18. An electrical energy storage/discharge device as claimed in claim 16, wherein said batteries are connected in parallel.

* * * * *